US012672913B2

(12) United States Patent
Prakash et al.

(10) Patent No.: US 12,672,913 B2
(45) Date of Patent: Jul. 7, 2026

(54) SYSTEM FOR DELIVERING HYPERTHERMIA TREATMENTS

(71) Applicant: Kansas State University Research Foundation, Manhattan, KS (US)

(72) Inventors: Punit Prakash, Manhattan, KS (US); Stefan H. Bossmann, Manhattan, KS (US); Sergio Curto, Rotterdam (NL)

(73) Assignee: Kansas State University Research Foundation, Manhattan, KS (US)

( * ) Notice: Subject to any disclaimer, the term of this patent is extended or adjusted under 35 U.S.C. 154(b) by 1171 days.

(21) Appl. No.: 16/093,774

(22) PCT Filed: Apr. 17, 2017

(86) PCT No.: PCT/US2017/027936

§ 371 (c)(1),
(2) Date: Oct. 15, 2018

(87) PCT Pub. No.: WO2017/181182

PCT Pub. Date: Oct. 19, 2017

(65) Prior Publication Data

US 2019/0125443 A1     May 2, 2019

Related U.S. Application Data

(60) Provisional application No. 62/323,152, filed on Apr. 15, 2016.

(51) Int. Cl.
*A61B 18/18*          (2006.01)
*A61B 18/00*          (2006.01)
(Continued)

(52) U.S. Cl.
CPC .......... *A61B 18/1815* (2013.01); *A61B 90/10* (2016.02); *A61N 1/403* (2013.01);
(Continued)

(58) Field of Classification Search
CPC ............... A61B 18/1815; A61B 90/10; A61B 2018/00023; A61B 2018/00577;
(Continued)

(56) References Cited

U.S. PATENT DOCUMENTS 4,397,314 A * 8/1983 Vaguine ............. A61B 18/1815
                                                                  607/104
5,540,737 A * 7/1996 Fenn ........................ A61N 5/02
                                                                  607/101

(Continued)

FOREIGN PATENT DOCUMENTS

WO      2015081210      6/2015
WO      2015136553      9/2015

OTHER PUBLICATIONS

Korkmaz, Erdal et al., "A Directive Antenna Array Applicator for Focused Electromagnetic Hyperthermia Treatment of Breast Cancer", Department of Electrical and Electronics Engineering, Fatih University, Lisbon, Portugal, pp. 4, 2015.

(Continued)

*Primary Examiner* — Adam Z Minchella
*Assistant Examiner* — Ashleigh Lauren Kern
(74) *Attorney, Agent, or Firm* — Hovey Williams LLP

(57) ABSTRACT

Apparatus for delivering in vivo hyperthermia treatments to a subject and methods of performing such treatments are provided. The apparatus comprises an imaging device, such as an MRI scanner, a microwave applicator, and a controller to target particular tissues within the subjects body for hyperthermia treatment. The microwave applicator emits microwave energy toward the target tissue and the imaging device provides real-time feedback as to the position of the applicator relative to the target tissues and thermometry data so as to permit real-time adjustment of the applicators operating parameters.

12 Claims, 18 Drawing Sheets

(51) Int. Cl.

| | |
|---|---|
| *A61B 90/00* | (2016.01) |
| *A61B 90/10* | (2016.01) |
| *A61N 1/40* | (2006.01) |
| *A61N 5/02* | (2006.01) |
| *G01R 33/28* | (2006.01) |
| *G01R 33/30* | (2006.01) |
| *G01R 33/48* | (2006.01) |

(52) U.S. Cl.
CPC ........... *A61N 5/025* (2013.01); *G01R 33/285* (2013.01); *G01R 33/307* (2013.01); *G01R 33/4808* (2013.01); *A61B 2018/00023* (2013.01); *A61B 2018/00577* (2013.01); *A61B 2018/00642* (2013.01); *A61B 2018/00702* (2013.01); *A61B 2018/00714* (2013.01); *A61B 2018/00791* (2013.01); *A61B 2018/00809* (2013.01); *A61B 2018/1823* (2013.01); *A61B 2018/1861* (2013.01); *A61B 2018/1869* (2013.01); *A61B 2018/1892* (2013.01); *A61B 2090/374* (2016.02)

(58) Field of Classification Search
CPC  A61B 2018/00642; A61B 2018/00702; A61B 2018/00714; A61B 2018/00791; A61B 2018/00809; A61B 2018/1823; A61B 2018/1861; A61B 2018/1869; A61B 2018/1892; A61B 2090/374; A61N 1/403; A61N 5/025; G01R 33/285; G01R 33/307; G01R 33/4808
See application file for complete search history.

(56) References Cited

U.S. PATENT DOCUMENTS

| | | | | |
|---|---|---|---|---|
| 5,769,879 | A * | 6/1998 | Richards | A61N 5/025 |
| | | | | 607/101 |
| 6,690,976 | B2 * | 2/2004 | Fenn | A61N 5/02 |
| | | | | 607/101 |
| 2007/0239062 | A1 * | 10/2007 | Chopra | A61B 5/4381 |
| | | | | 600/549 |
| 2008/0114274 | A1 * | 5/2008 | Moonen | A61N 7/02 |
| | | | | 601/3 |
| 2008/0228063 | A1 * | 9/2008 | Turner | A61N 5/02 |
| | | | | 600/411 |
| 2010/0100092 | A1 * | 4/2010 | Turner | A61B 18/1815 |
| | | | | 606/33 |
| 2012/0141381 | A1 * | 6/2012 | Dewhirst | A61K 49/1812 |
| | | | | 264/4.3 |
| 2014/0300354 | A1 | 10/2014 | He et al. | |
| 2015/0265216 | A1 | 9/2015 | Andrews | |

OTHER PUBLICATIONS

Wu, Liyong et al., "An RF Phased Array Applicator Designed for Hyperthermia Breast Cancer Treatments", Department of Electrical and Computer Engineerig, Michigan State University, East Lansing Michigan, 48824, USA, pp. 25; Jul. 8, 2008.
Asili, Musrafa et al., "Flexible Microwave Antenna Applicator for Chemo-thermotherapy of the Breast", IEEE Antennas and Wireless Propagations Letters, pp. 4, 2015.
International Search Report and Written Opinion dated Aug. 22, 2017, in PCT/US2017/27936, filed Apr. 17, 2017.
Kowalski, Marc E. "Optimization of Electromagnetic Phased-Arrays for Hyperthermia via Magnetic Resonance Temperature Estimation," IEEE Transactions on Biomedical Engineering, Nov. 2002, vol. 49, No. 11.
Mcwilliams, Brogen T. "A Directional Interstitial Antenna for Microwave Tissue Ablation: Theoretical and Experimental Investigation," IEEE Transactions on Biomedical Engineering, Sep. 2015, vol. 62, No. 9.

* cited by examiner

Inflow

Outflow (c)

(f)

(b)

(e)

(a)

(d)

(a)                    (b)

SYSTEM FOR DELIVERING HYPERTHERMIA TREATMENTS

RELATED APPLICATIONS

This application is a National Stage Entry under 35 U.S.C. 371 of International Patent Application No. PCT/US2017/027936, filed Apr. 17, 2017, which claims the benefit of U.S. Provisional Patent Application No. 62/323,152, filed Apr. 15, 2016, each of which is incorporated by reference herein in its entirety.

FEDERALLY SPONSORED RESEARCH OR DEVELOPMENT

This invention was made with government support under grant CBET 1337438 awarded by the National Science Foundation. The United States government has certain rights in the invention.

BACKGROUND OF THE INVENTION

Field of the Invention

The present invention is generally directed toward systems for delivering targeted hyperthermia treatments to tissues of the body of a subject and methods of providing such hyperthermia treatments. In particular, the present invention utilizes an imaging device, such as a magnetic resonance imaging (MRI) scanner, and a microwave applicator to target particular tissues within the subject's body for hyperthermia treatment and to provide real-time feedback permitting real-time adjustment of the microwave applicator's output and direction of microwave emission.

Description of the Prior Art

Microwave ablation (MWA) is an increasingly used thermal therapy modality for minimally-invasive treatment of tumors and benign disease. Other energy sources for thermal ablation include radiofrequency current, lasers, catheter-based ultrasound applicators, chemical, and cyroablation. These procedures may be performed minimally invasively, typically under guidance of ultrasound, or computerized tomography guidance, or under open surgery. MWA has found clinical applications in the treatment of tumors in the liver, kidney, lung, and bone, as well for treatment of cardiac arrhythmias, ablation of benign prostate tissue to treat hyperplasia (BPH), ablation of the uterine endometrial lining to treat menorrhagia, ablation of the esophageal wall for treating Barrett's esophagus and GERD, ablation of nerves for treating back pain, and ablation of renal nerves for treating chronic high blood pressure.

During an ablation procedure, an antenna is inserted into the target tissue, and radiates electromagnetic energy at microwave frequencies; most currently available devices operate within frequency bands approved for industrial, scientific, and medical (ISM) use, centered at 915 MHz and 2.45 GHz. Electromagnetic energy radiated from the antenna is deposited in the electromagnetic lossy tissue leading to heating via dielectric hysteresis. While thermal damage following ablation is a complex function of the time-temperature history during heating, temperatures in excess of 60° C. lead to near-instantaneous cell death by coagulative necrosis. Irreversible, but not lethal, thermal damage may occur in cells heated above 42° C. A fundamental principal of successful ablation is the creation of an ablation zone that sufficiently covers the entire tumor while providing a margin of safety for adjacent tissues.

In most microwave ablation procedures, the antenna is inserted into the center of the targeted tissue, and the ablation zone grows radially outward. When ablating targets in proximity to critical structures, caution must be taken to ensure complete thermal coverage of the target volume, while precluding thermal damage to non-targeted tissues. Fluid installation between the target site and organs at risk of injury has emerged as a practical technique for minimizing heating of non-targeted tissues. Conventional microwave ablation antennas are based on coaxial antenna designs, have axially symmetric radiation patterns, and do not offer control of the energy deposition pattern in the angular expanse. Spatial control of the energy deposition pattern is limited to control of heating along the antenna length, achieved by employing a sleeve/choke. While multiple antennas operated as a phased-array may offer some limited steering of power deposition, the increased invasiveness and system complexity are drawbacks compared to the use of single applicators.

Hyperthermia can also be used for inducing biological effects that synergize with other therapeutic modalities, such as the heat-triggered release of therapeutic agents. The biological effects that are induced by hyperthermia are a function of time-temperature history, i.e., a "thermal dose." Heterogeneity in blood flow and tissue physical properties may lead to highly variable thermal doses for the same energy delivery parameters.

Therefore, in addition to better guidance for avoiding damage to healthy tissues during microwave ablation procedures, there is a need for addressing in vivo heterogeneity in order to deliver an appropriate thermal dose for each patient.

Breast cancer is the most frequent cancer among women; in 2013, accounting for 29% of all new cancer diagnoses amongst women in the USA. Early detection is crucial in the control of the disease, with the rationale that if the tumor is detected when still entirely localized within the breast, complete excision through mastectomy or lumpectomy may be curative. Lumpectomy or breast conserving surgery is a standard treatment alternative to mastectomy (or total removal of a breast) for some patients with tumors under 4 cm. For a large number of patients, mastectomy/lumpectomy is preceded or followed by radiotherapy and/or chemotherapy.

While a large proportion of tumors arise in the upper outer quadrant of the breast, breast carcinomas can develop in any location of the breast. Tumor location and size are determinant factors to classify the cancer staging. Breast cancer stage II comprises tumor sizes between 2 cm to 5 cm in the larger diameter.

Waveguide applicators have been employed for the treatment of breast cancer recurrences. With the clinical acceptance of breast conserving surgery as a less aggressive treatment option than standard mastectomy, minimally invasive techniques have arisen. Methods for delivering microwave hyperthermia to the intact breast with the objective of focusing energy within the tumor include a deformable mirror approach and metamaterial lens. In order to steer energy at different locations of the breast, various approaches have been considered, such as a system that compresses the breast target and delivers energy with multiple elements, a rigid cylindrical array of patch antennas, a 2D model with point source antennas to focus energy in targeted volumes, arrays of tapered slot-antennas, and a 4-element phased array system operating at 140 MHz, a 1.6

GHz 9-element constant phase system for the treatment of tumors located close to the skin's surface.

Single element antennas have also been proposed, but while these applicators offer the advantage of simplified practical implementation and treatment delivery, they afford limited spatial control of energy deposition patterns. Systems incorporating multiple antenna elements enable improved spatial control of energy, but the system operating frequency must be selected to balance: antenna dimensions, focal zone size, coupling between antenna elements, and the ability to treat deep-seated targets.

SUMMARY OF THE INVENTION

According to one embodiment of the present invention there is provided a system for delivering hyperthermia treatments to the body of a subject. The system comprises a microwave applicator configured for emitting electromagnetic energy therefrom sufficiently strong to cause tissue ablation within the subject. The system also comprises a magnetic resonance imaging scanner operable to receive at least a portion of the subject's body and generate an internal image of the at least a portion of the subject's body and provide thermometry data for the at least a portion of the subject's body. The system further comprises a controller operable to analyze, in real time, at least two images received from the scanner and to generate a signal used to control the amount of and/or direction of electromagnetic energy emitted from the applicator.

According to another embodiment of the present invention there is provided a method of delivering hyperthermia treatments to the body of a subject. The method comprises positioning at least a portion of the subject's body within a magnetic resonance imaging scanner that is operable to generate an internal image of the at least a portion of the subject's body and provide thermometry data for the at least a portion of the subject's body. A microwave applicator is positioned adjacent to tissue within the subject's body that is targeted for ablation. The microwave applicator is configured for emitting electromagnetic energy therefrom sufficiently strong to cause ablation of the tissue. Electromagnetic energy is emitted from the applicator and directed toward the tissue targeted for ablation thereby heating the tissue. At least a portion of the subject's body is imaged with the magnetic resonance imaging scanner and thermometry data for the imaged portion of the subject's body is generated. The image and thermometry data is transmitted to a controller that is operable to analyze, in real time, the image received from the scanner, and a signal is generated that is used to control the amount of electromagnetic energy emitted from the applicator. The method also comprises analyzing, with the controller, the image received from the scanner, and generating, with the controller, a signal. The signal is used to control the amount of and/or direction of electromagnetic energy emitted from the applicator.

BRIEF DESCRIPTION OF THE DRAWINGS

FIGS. 9(*c*) and (*d*) depict a large breast model with a target located in the breast center and near the chest wall phantom, respectively;

FIG. 13(*b*) is a schematic representation of the experimental phased antenna array detailing the position of the temperature probes;

DETAILED DESCRIPTION OF THE PREFERRED EMBODIMENT

Moderate tissue heating is the subject of significant investigation with application to thermally mediated delivery and/or heat-triggered release of therapeutic agents (e.g. drugs, immune stimulatory agents) for treatment of cancer and benign disease. Ultra-high field magnetic resonance imaging (MRI) provides high-resolution (spatial and temporal) imaging of the tumor environment and vasculature. Certain embodiments of the present invention pertain to microwave hyperthermia systems that are integrated with an MRI scanner, such as an ultrahigh field MRI scanner, to facilitate real-time monitoring of physical and physiological changes induced by hyperthermia with submillimeter resolution in conjunction with MR thermometry.

In one embodiment, the system incorporates a microwave hyperthermia applicator that can be positioned adjacent to a target, animal or human, and directing microwave energy for localized treatment of tumors within the target. In certain embodiments, the applicator may be constructed as described in PCT/US2015/063210, incorporated by reference herein in its entirety. FIGS. 1-4 schematically depict an applicator device 10 in accordance with one embodiment of the present invention. Device 10 generally comprises a transmission line 12 that is configured for transmitting an electromagnetic signal from a signal generator, described in further detail below. As more clearly shown in FIGS. 2-4, the transmission line 12 is a coaxial cable that comprises an inner conductor 14 and an outer conductor 16 and a dielectric material 18 disposed therebetween. In certain embodiments, the inner conductor 14 comprises copper, silver, gold, silver-plated copper weld, or any combination thereof, and the outer conductor 16 comprises a conductive metal, for example, copper. In the case of a flexible device 10, outer conductor 16 may be a woven metallic (e.g., copper) shield. The dielectric material 18 may comprise, for example, polytetrafluoroethylene, air, polyethylene, alumina, nylon, and combinations thereof.

Figure 1:
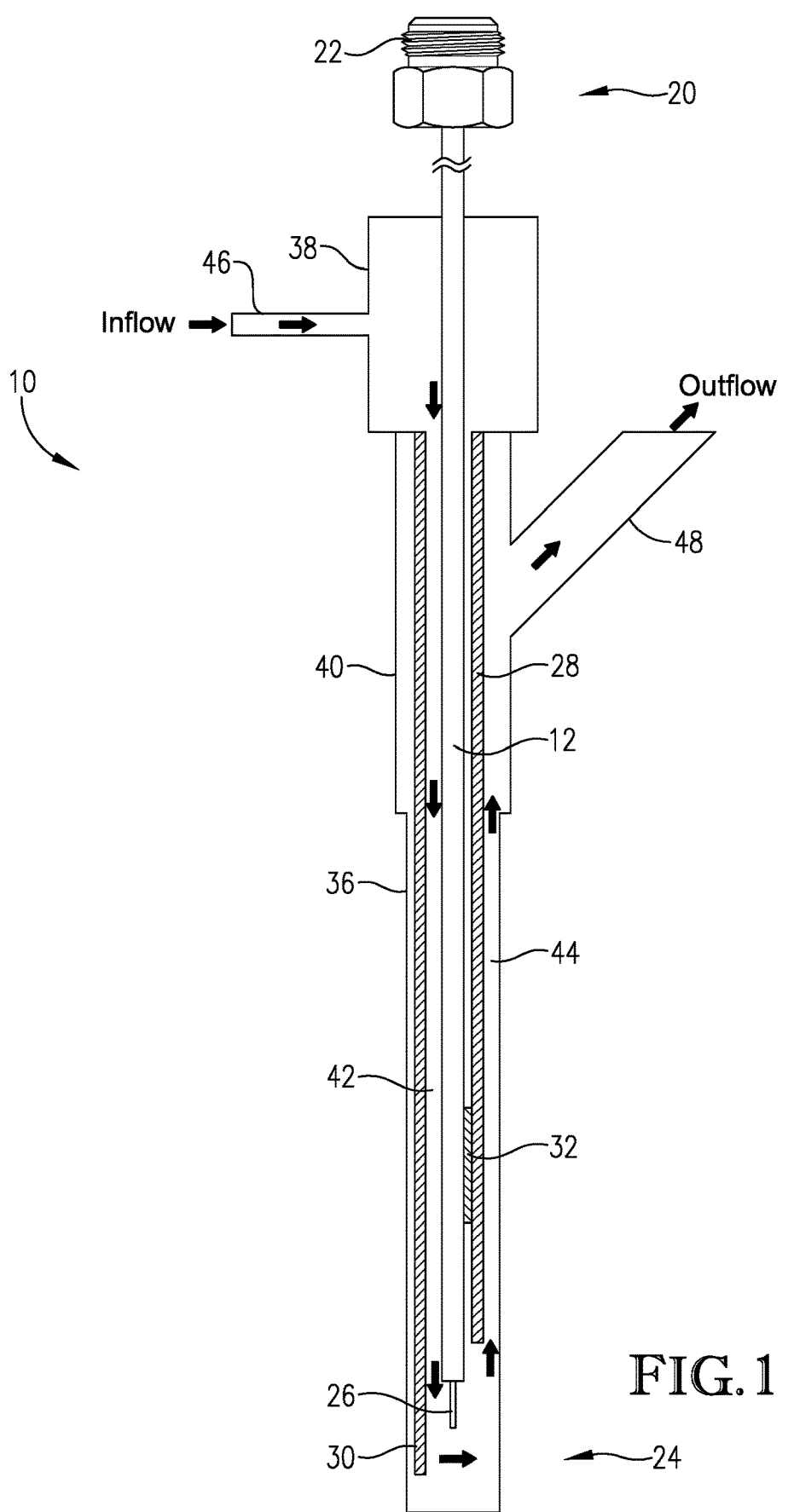
FIG. 1 is a schematic diagram of a microwave applicator device that may be used with certain embodiments of the present invention.

As shown in FIG. 1, the proximal end 20 of transmission line 12 comprises an SMA connector 22 or other structure (e.g., N-type and BNC connectors) that is suitable for connecting the transmission line to the signal generator. The distal end 24 of transmission line 12 comprises a portion of the line in which the outer conductor 16 and dielectric material 18 have been removed so as to form an antenna 26 that is operable to emit electromagnetic energy therefrom, which is sufficiently strong to cause tissue ablation. In certain embodiments, antenna 26 comprises a monopole antenna; however, other types of antenna configurations, such as dipole, slot, and helical antennas, may also be used without departing from the scope of the present invention.

Figures 2, 3, 4:
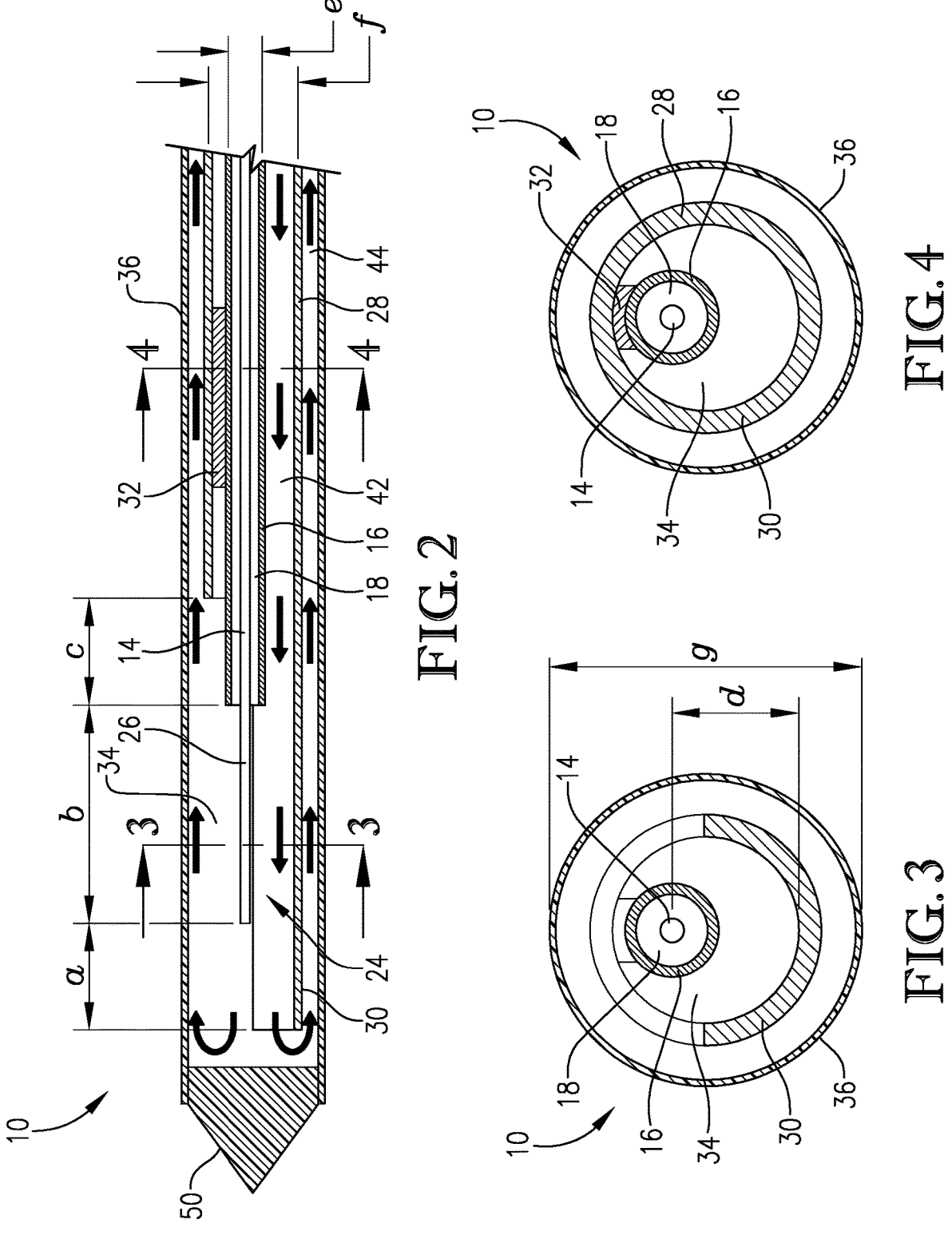
FIG. 2 is a cross-sectional view of the distal end of the applicator device of FIG. 1.
FIG. 3 is a cross-sectional view of the applicator device taken along line 3-3 of FIG. 2.
FIG. 4 is a cross-sectional view of the applicator device taken along line 4-4 of FIG. 2.

The transmission line 12 is secured within an inner tubular member 28. As illustrated in FIG. 2, a portion of the distal end of tubular member 28 has been removed so as to form a hemicylindrical reflector 30. Because a portion of tubular member 28 is utilized to create reflector 30, tubular member 28 comprises an electrically-conductive material, such as stainless steel, silver, copper, gold, and other metals and alloys. In other embodiments, reflector 30 is made from any material with high electrical conductivity ($\sigma > \sim 10^4$ S/m). It is within the scope of the present invention for the reflector to comprise alternate configurations, including different shapes and to be fabricated from a material that is different than tubular member 28. For example, reflector 30 may be rectilinear as opposed to the curvilinear configuration illustrated in FIG. 3. Reflector 30 need not have a uniform cross-sectional configuration as the configuration could change along the length of the reflector.

In certain embodiments in which reflector 30 comprises a hemicylindrical shape, the reflector has an arc angle, $\theta$, that is equal to 180° or less, or less than 160°, or less than 140°.

In other embodiments, $\theta$ is from about 80° to about 200°, or from about 100° to about 180°, or from about 120° to about 140°. As illustrated in FIG. 3, $\theta$ is equal to approximately 180°, and is defined as the angle than an arc makes at the center of the circle of which it is a part. Selection of $\theta$ affects the impedance matching between antenna 26 and transmission line 12 which also impacts the observed radial extent of the ablation zones in a forward direction (r), in a reverse direction (r'), and the width of the ablation zone (w).

In certain embodiments, the relative positioning of transmission line 12 (and antenna 26) within tubular member 28 is maintained by one or more brackets 32. Bracket 32 may comprise a non-conducting material so that tubular member 28 (and reflector 30) is not electrically coupled with outer conductor 16. However, it is within the scope of the present invention for bracket 32 to comprise an electrically conductive material, such as a metal. In alternate embodiments, bracket 32 need not be used. Rather, an adhesive may be used to affix transmission line 12 to the inner wall of tubular member 28.

A dielectric material 34 surrounds antenna 26 and is disposed between the antenna and reflector 30. In certain embodiments, dielectric material 34 is different than dielectric material 18 that comprises transmission line 12. In particular embodiments, dielectric material 34 has a significantly greater dielectric constant than dielectric material 18. As explained below, the selection of dielectric material 18 plays a role in the selection of a relative positioning of antenna 26 and reflector 30 (d in FIG. 3) so as to achieve an optimal impedance matching and avoid undesirable energy loss and heat generation. In certain embodiments, dielectric material 34 comprises a material selected from the group consisting of water and metal oxides, such as titanium dioxide. In other embodiments, dielectric material 34 has a relatively high dielectric constant, preferably greater than 20, greater than 50, or greater than 75. In still other embodiments, dielectric material 34 does not comprise a thermoplastic or elastomeric material such as an epoxy, polyethylene, polytetrafluoroethylene (PTFE), polyether block amide, polyetherimide, polyimide-based polymers, or a ceramic material, as these materials tend to exhibit very low dielectric constant values (e.g. PTFE has a dielectric constant of 2.1).

Device 10 further comprises an outer, non-electrically conductive tubular body 36 inside of which at least reflector 30 and the antenna 26 are received. As the microwaves emitted from antenna 26 must pass through tubular body 36 in order to reach the tissue targeted for ablation, in certain embodiments tubular body 36 comprises an elastomeric or plastic material such as polyimide, PTFE, and polyether ether ketone (PEEK) tubing. This construction, as opposed to be formed from an electrically conductive material such as metal, also reduces adhesion of ablated tissue to device 10 during use thereby facilitating easier insertion and withdrawal of the device into and from the patient's body. As illustrated in FIG. 1, tubular body 36 may be connected to a number of peripheral fittings such as a hemostasis valve 38 and Y-adapter 40 in order to circulate a cooling fluid within device 10 in order to dissipate heat that is generated during operation. Tubular body 36 may also be utilized in the formation of reflector 30. For example, instead of being an extension of tubular member 28, reflector 30 may comprise a highly conductive coating material, such as an epoxy or metallic paint, that is applied across a portion of the interior surface of the distal end of tubular body 36 at the desired arc angle. Such a configuration can be used to substantially decrease the overall diameter for device 10.

The transmission line 12 and tubular member 28 cooperate to define an innermost annular region 42 into which the cooling fluid may be directed from hemostasis valve 38 and Y-adapter 40. Tubular member 28 and tubular body 36 cooperate to define an outermost annular region 44. The innermost annular region 42 is configured to conduct a cooling fluid that is introduced into the device via an inlet 46 of hemostasis valve 38 in a first direction toward the distal end of the tubular member 28. The outermost annular region 44 is configured to conduct the cooling fluid in a second direction away from the distal end of tubular member 28 and toward an outlet 48 formed in Y-adapter 40.

The cooling fluid circulated within device 10 can be any appropriate fluid for transferring heat from the various components making up device 10. The cooling fluid cools device 10 thereby precluding thermal damage to non-targeted tissue along the length of the device. In certain embodiments water is a preferred cooling fluid. However, it is within the scope of the present invention for other cooling fluids to be used such as saline, FLUORINERT, liquid chlorodifluoromethane, nitrous oxide, nitrogen, carbon dioxide and air.

An advantage of certain embodiments of the present invention is that the cooling fluid being conducted within annular region 42 may also comprise the dielectric material 34 that surrounds antenna 26 and is located between the antenna and reflector 30. Thus, in these embodiments, the cooling fluid serves two functions: removal of undesirable heat generated during operation of device 10 and as the dielectric material 34 through which the microwave energy emitted by antenna 26 passes.

In certain embodiments of the present invention, to facilitate direct percutaneous insertion, device 10 may be equipped with a sharp, rigid catheter tip 50. In certain embodiments, tip 50 may be attached to the distal end of reflector 30. In other embodiments of the present invention, device 10 can readily be integrated with flexible coaxial cable for endoscopic, endoluminal, or endovascular targeting of structures. In such embodiments, tubular body 36 may comprise a balloon or other highly flexible and resilient structure. In certain embodiments, device 10 may be equipped with some type of steering mechanism that permits a physician to direct the distal portion of the device to a proper endoluminal location.

As noted above, impedance matching between transmission line 12 and antenna 26 can be achieved through selection of dielectric material 34 and a number of structural configurations for reflector 30 and antenna 26. It has been discovered that impedance matching between the antenna 26 and transmission line 12, as indicated by the calculated antenna reflection coefficient $(S_{11})$, can be achieved, at least in part, by selective positioning of antenna 26 and reflector 30. In particular, it has been discovered that a low antenna reflection coefficient could be achieved when the antenna-reflector spacing, d, was from about $\frac{1}{12}$ to about $\frac{1}{8}$ of a wavelength of the electromagnetic energy emitted from the antenna. More preferably, this distance is approximately $\frac{1}{10}$ of a wavelength. In certain embodiments, over the frequency range 2-3 GHz, the following relationship holds between d (in mm) and wavelength $\lambda$ (in mm): $d=0.60\lambda-7.02$. This distance, d, as labeled in FIG. 3 is measured from the center of the antenna to the inner wall of the reflector at its center point (e.g., in the case of a hemicylindrical reflector, the midpoint of its arc length).

The wavelength of electromagnetic energy emitted from antenna 26 is dependent, at least in part, upon the dielectric constant value of the dielectric material 34 surrounding the antenna. In certain applications, such as where device 10 will be used endovascularly or percutaneously, it can be advantageous for device 10 to be as narrow as possible. Selecting a dielectric material 34 with a high dielectric constant will produce shorter wavelengths, and hence, a smaller d value can be used and still achieve a desirable degree of impedance matching. In other applications, such as where device 10 will be used endoscopically, the device size can be greater (and have a greater d value) and thus a dielectric material 34 with a lower dielectric constant can be used. For example, in certain embodiments where a small device size is required, the dielectric material 34 may comprise a metal oxide material, which can have a dielectric constant of greater than 100 and produce very short wavelengths. In other embodiments, where a larger device size can be tolerated, the dielectric material 34 can be water, which has a dielectric constant of 78.6 at 2.45 GHz, and the device can also enjoy the benefits of water cooling as described above.

The selection of a d value can influence the structural relationship between the antenna and other parts of device 10 besides reflector 30. In certain embodiments, antenna 26 has a longitudinal axis that is offset from, but parallel to, the longitudinal axis of device 10. This offset may be in a direction towards or away from reflector 30. In other embodiments, the longitudinal axis of antenna 26 may be coaxial with the longitudinal axis of device 10. In still other embodiments, the longitudinal axis of antenna 26 may be transverse to the longitudinal axis of device 10. In certain embodiments in which antenna 26 is formed from the inner conductor 14 of transmission line 12, the antenna can be bent out of coaxial alignment with the inner conductor to achieve the desired d value. This structural relationship between antenna 26 and various portions of device 10 is also another variable that can be used to achieve the desired impedance matching between the antenna and transmission line 12.

It has been discovered that the arc angle, $\theta$, of the reflector 30 can also have an effect on the antenna reflection coefficient $(S_{11})$ and the extents of the ablation zone, characterized by the dimensions r (radial extent of the ablation zone in the forward direction), r' (radial extent of the ablation zone in the reverse direction), and w (width of the ablation zone). In certain embodiments, it is desirable to select $\theta$ to as to provide a low $S_{11}$ value, but also to minimize r' so as to avoid damage to non-targeted tissue. In other embodiments, it may be desirable to select $\theta$ so as to provide a low $S_{11}$ value, but maximize r so as to provide as deep of an ablation zone into the targeted tissue as possible.

Because effective impedance matching between the antenna 26 and transmission line 12 can be achieved through the control of a number of structural variables, such as dielectric material 34 selection, $\theta$, and d, device 10 can be constructed without using an impedance matching device between transmission line 12 and antenna 26. Common impedance matching devices used to place the antenna structure in resonance increase the efficiency thereof include capacitors, resistors, inductors, stub tuners, stub transmission lines, or any combination thereof, whether in series or in parallel with the antenna.

Figure 5:
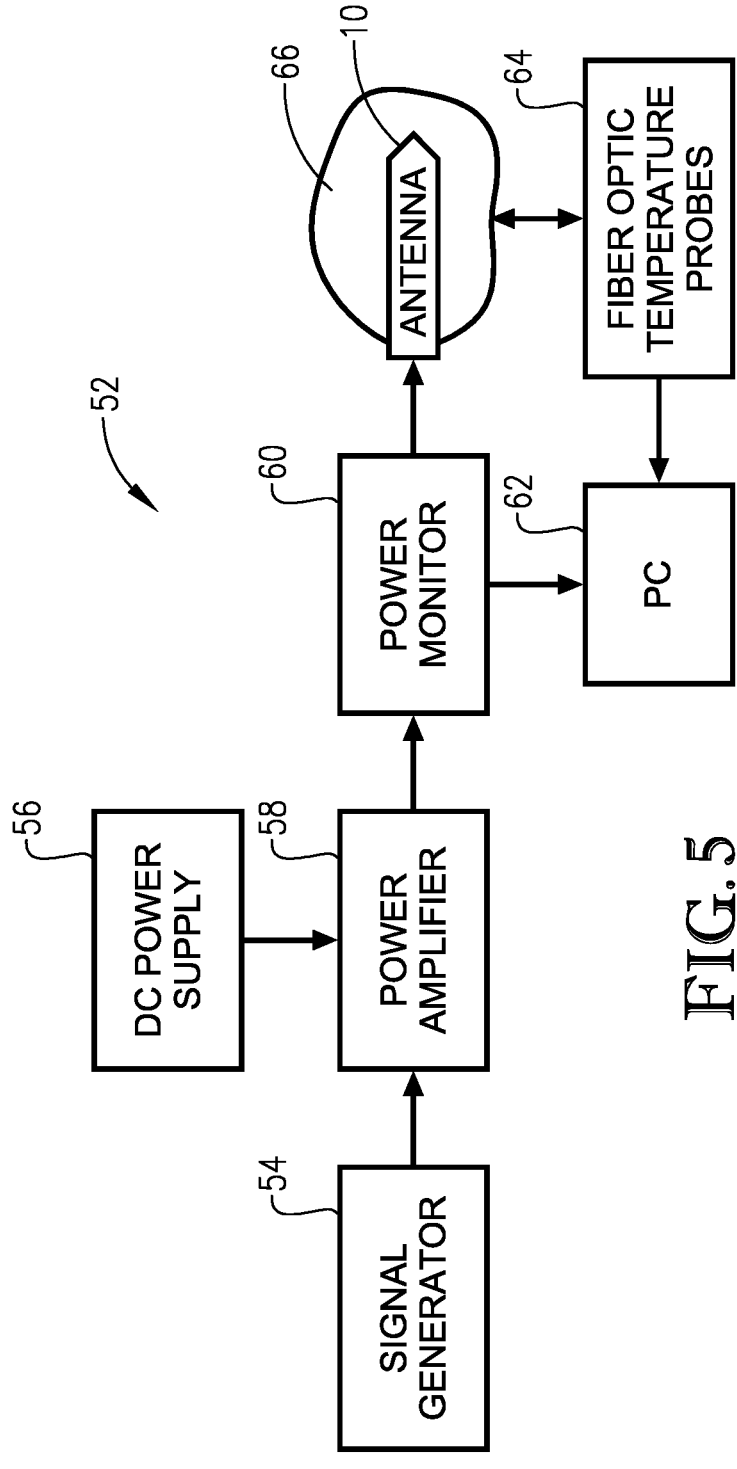
FIG. 5 is a schematic diagram of an embodiment of a microwave applicator device including a power supply, signal generator and antenna.

FIG. 5 schematically depicts an exemplary electrosurgical device 10 constructed in accordance with one embodiment of the present invention. An electromagnetic power source 52 is used to generate and transmit the desired microwave energy to device 10. Electromagnetic power source 52 may include a microwave signal generator 54, and optionally a DC power supply 56, a power amplifier 58, and a power monitor 60. The operation of device 10 and the various pieces of equipment utilized by power source 52 may be monitored and controlled by a microprocessor 62, such as a personal computer or a handheld device. In certain embodiments, the frequencies generated by the signal generator are similar to those that are associated with the frequencies typically used to heat water. In particular embodiments, the frequencies generated range from about 800 MHz to 6 GHz, from about 900 MHz to about 5 GHz, or from about 1 GHz to about 3 GHz. In preferred embodiments, particularly for devices used for experimental clinical work, the frequencies generated are 915 MHz or 2.45 GHz. Optionally, temperature probes 64 can be inserted into the tissue 66 along with device 10 so as to monitor the temperature of tissue being ablated and adjacent to the tissue being ablated.

As described above, antenna 26 is designed to have an impedance close to that of the transmission line 12 from signal generator 54 (nominally, 50Ω) at the operating frequency. The impedance presented by antenna 26 is a function of the dimensions of the antenna as well as the wavelength at the operating frequency. Because of this impedance matching, device 10 can be used in methods of treating body tissues that are in close proximity to critical structures. Device 10 is configured to emit microwave energy toward the targeted tissue with a directional radiation pattern. The physician or operator of device 10 may orient the device such that energy is emitted substantially toward the target structure and away from the critical tissues that should not be damaged. In such applications, a physician may orient the antenna towards the target structure, and away from the critical tissues that should not be damaged. Device 10 can be applied to target tumors in regions that can be accessed percutaneously, endoluminally (e.g., bronchii, urethra, rectum, stomach, esophagus) or endovascularly (e.g., renal nerves). Device 10 may also be used for moderate heating of tissues (e.g., between about 41 and 44° C.) as an adjuvant to radiation and or chemotherapy for treatment of select cancers.

Device 10 can be used in connection with sensing or imaging equipment configured to give real-time feedback to the physician conducting a procedure. In certain embodiments, the sensing or imaging equipment can give the physician information regarding the ablation boundary associated with the use of device 10. If the ablation boundary does not extend to the edge of the desired target, the physician can rotate device 10 to treat the full extent of tissue in between the desired margins. For example, device 10 can be fabricated from MRI-compatible materials for use under MRI guidance. Such MRI-compatible materials include non-ferromagnetic materials such as aluminum, titanium, brass, and copper. Such devices do not generate a visible imaging artifact when introduced into an MRI bore. Use of device 10 with an MRI offers the benefit of real-time volumetric temperature imaging for feedback controlled procedures. For instance, when targeting structures in very close proximity to several critical structures, MRI temperature imaging could be used to assess when the treatment boundary extended to the edge of the desired target, and then guide rotation of the device to target tissue in another direction.

In certain embodiments, the MRI scanner used with the present invention comprises at least a 1.5 tesla scanner, and preferably at least a 3 tesla, at least a 7 tesla, or at least a 14 tesla scanner. In particularly preferred embodiments, the MRI scanner is an ultra-high field scanner.

In certain embodiments, an image-based feedback controller is used as a part of an MRI-guided system for delivering hyperthermia treatments to a subject. The subject is placed within an MRI scanner along with a microwave applicator operable to deliver microwave energy to selected tissues of the subject. The applicator can be placed within the subject's body, such as percutaneously, endoluminally, or endovascularly, or the applicator can remain outside, but adjacent to the subject's body.

The MRI scanner is activated and the operator is provided an image of the subject and target tissues as well as the location of the applicator relative thereto. Thus, the MRI scanner facilitates precise localization of the applicator relative to the target tissue. Once properly positioned relative to the target tissues, the applicator can be switched on and deliver microwave energy to the target tissues. During delivery of the hyperthermia treatment, the operator can monitor, in real time, the effectiveness of the treatment using the MRI scanner to detect the temperature of the affected tissues. The MRI scanner can provide real-time temperature measurements based upon temperature sensitive MR parameters such as the proton resonance frequency (PRF). Temperature sensitive contrast agents could also be used to aid in this real-time temperature monitoring.

In another embodiment, the MRI scanner can be used to monitor another parameter associated with the subject's body, and particularly, the area of the subject's body receiving the hyperthermia treatment. For example, the blood flow to the area of the subject's body undergoing hyperthermia treatment can be monitored. The controller can be used to analyze images received from the MRI scanner pertaining to the blood flow pattern to the affected area and adjustments made to the microwave applicator to achieve a desired blood flow pattern.

Figure 6:
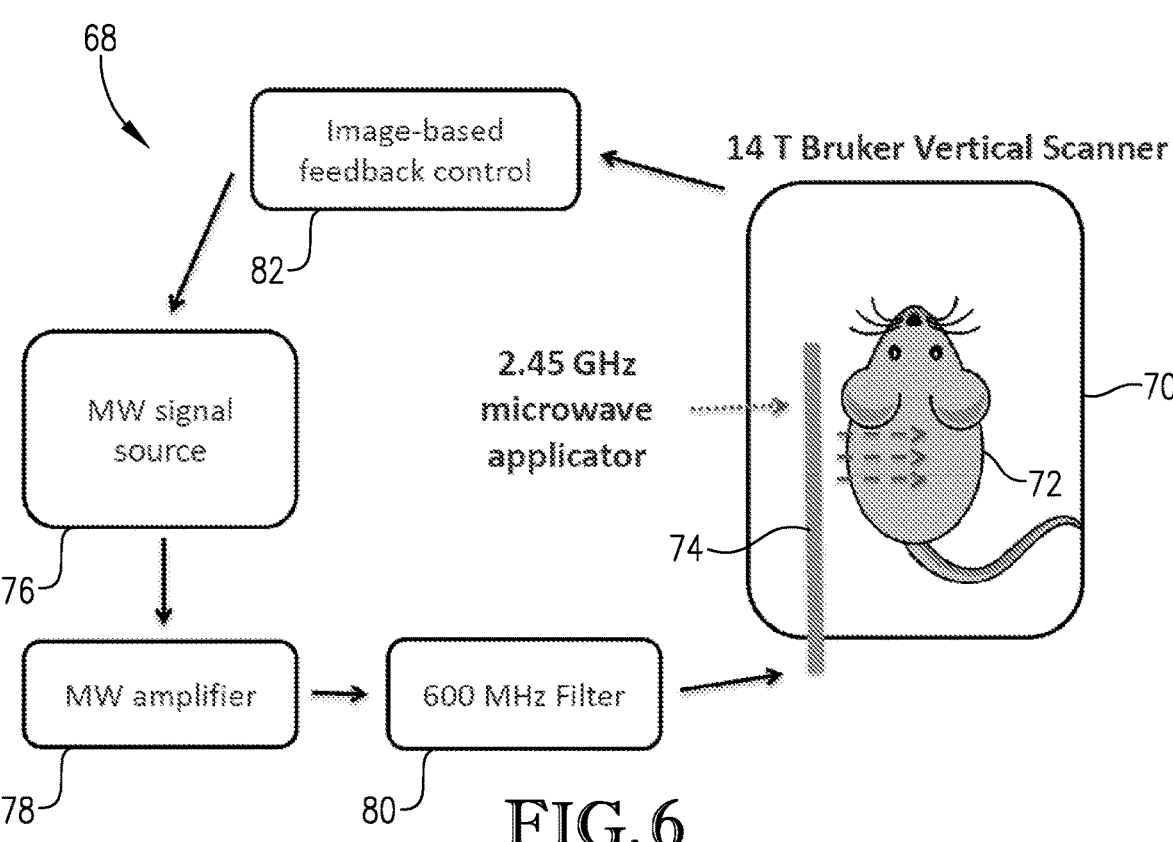
FIG. 6 depicts an exemplary hyperthermia delivery platform.

FIG. 6 schematically depicts an MRI-guided system 68 constructed in accordance with the present invention. System 68 comprises a 14T Bruker Vertical MRI scanner 70, which as illustrated, is sized to receive a small animal 72, such as a mouse, therein. A microwave applicator 74 is also placed within scanner 70 adjacent to the animal 72. A microwave signal source 76 is used to generate microwaves, which are then amplified by an amplifier 78. The amplified microwaves and then passed through a 600 MHz filter 80 before being delivered to the applicator 74 operating at 2.45 GHz. The scanner 70 provides real-time images of the animal 72 and applicator 74, and in particular of temperatures within the tissues of the animal 72 during application of the microwaves. A controller 82 receives the images generated by the scanner 70 and, based on those images, adjusts the output of the microwave signal source 76 to deliver prescribed temperature/thermal dose profiles.

The image generated by the MRI scanner can also be used to adjust the position of the microwave applicator 74. In certain embodiments, the applicator 74 may be positioned outside of the subject's body. However, it is also within the scope of the present invention for the applicator to be positioned within the subject's body. For example, the applicator 74 can be inserted within the subject's body percutaneously, endoluminally, or endovascularly. As ablation of the target tissue progresses, the real-time data provided by the MRI scanner 70 can be used to adjust the position of the applicator 74 and/or change the direction of the radiated microwave energy in the case of a directional applicator so as to fully ablate the target tissue.

The thermometry data generated by the MRI scanner can be used to discern the temperature profile within the tissue undergoing ablation, as well as any surrounding, healthy tissue. As tissues within a body can be heterogenous, adjustment of the applicator output may be required to achieve the desired effect. For example, if the thermometry data shows heating of the healthy tissue that is above acceptable levels, the signal generated by the controller 82 can be used to command a reduction in electromagnetic energy emitted from the applicator. If the thermometry data shows heating of the healthy tissue is below acceptable levels, the signal generated by the controller 82 may be used to command an increase in the electromagnetic energy emitted from the applicator 74 so as to accelerate the ablation process. Additional temperature control can be achieved by circulating a cooling fluid within the applicator itself.

In certain embodiments, the system is operable to deliver hyperthermia (moderate tissue heating, temperatures of approximately 40-45° C. to selected tissues of a subject under ultra-high field MRI guidance. This is achieved through the design and integration of a directional microwave antenna that fits within the bore of the scanner, and is positioned adjacent to or within the body of the subject. Microwave energy is supplied to the device, with in-line electrical filters installed to prevent electrical interference between the MRI scanner and the antenna. Real-time MR thermometry and other imaging sequences can then be used to control the delivery of electromagnetic energy to yield a desired therapeutic effect. Embodiments of the present invention may be useful in preclinical research applications involving hyperthermia, such as the thermally triggered release of drugs and other therapeutic agents, thermal sensitization of radiation/chemotherapy, and heat-induced bioeffects. The ability to simultaneously image during heating at ultra-high fields enables high-resolution monitoring of physical and physiological changes induced by heating.

Certain MRI scanners, such as those used for small animals, have small bore sizes (about 3 cm) relative to the subject (about 2 cm). Thus, the hyperthermia delivery applicators used with the system should be compact so as to fit within the limited space of the MRI scanner bore. In large animal and human MRI scanners, applicator size is less of an issue. Regardless, any imaging artifacts due to the instrument need to be confined to a very small region, so as not to impact the imaging field of view. The microwave applicator used in certain embodiments of the present invention affords sufficient electromagnetic penetration (antenna operates at 2.45 GHz) to heat targets within the subject, while affording thermal sparing of surface tissues.

In another aspect of the present invention, wearable hyperthermia system for delivering hyperthermia to tumors within breast tissue is provided. This hyperthermia system comprises a phased antenna array including a plurality of antenna elements with a shared groundplane. Exemplary arrays are described in the Examples below.

EXAMPLES

The following examples depict apparatus and methods in accordance with certain embodiments of the present invention. It is understood that these examples are provided by way of illustration only and should not be taken as limiting of the scope of the present invention.

Example 1

Figure 7:
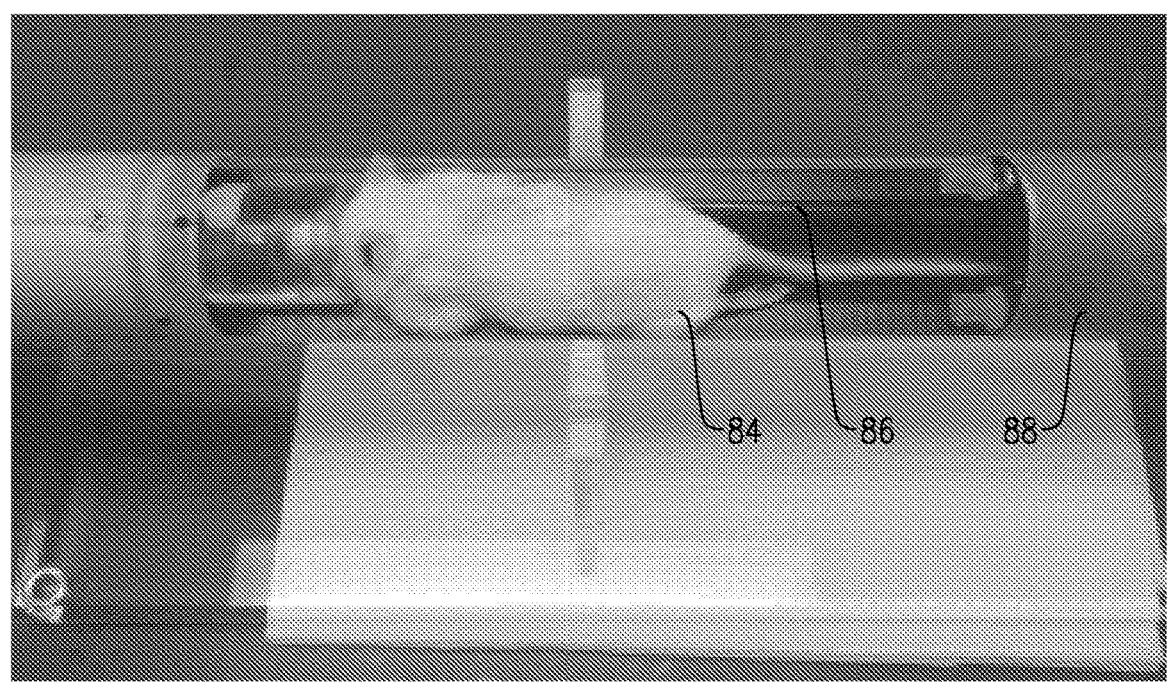
FIG. 7 is a photograph depicting a mouse positioned inside a micro-imaging probe.

In this example, a 3D electromagnetic-bioheat transfer model was used to optimize a directional 2.45 GHz antenna adjacent to the small-animal and inside the bore (30 mm diameter) of a 14 T ultra-high field MRI scanner (Bruker Avance III). The antenna was constructed of MRI compatible materials as described above having a length of 3 ft. and a 3.5 mm outer diameter. The radiating tip of the antenna was approximately 6 mm in length. Water was circulated within the antenna for cooling purposes. Optimization objectives were: device miniaturization, impedance matching, and heating rate/profile of the target volume. The hyperthermia delivery device was fabricated from MR-compatible materials and integrated within the MR environment with band-pass filters (2.4 GHz±100 MHz) inserted in-line to mitigate any electrical interference between the scanner and the antenna. The experimental setup is schematically depicted in FIG. 6. FIG. 7 is a photograph depicting a mouse 84 placed within a micro-imaging probe 88. The microwave applicator 86 is shown positioned adjacent to the mouse's body. Impedance matching and heating performance were measured in tissue mimicking agar-based phantoms and ex vivo tissue. FLASH and EPI MR sequences were investigated for monitoring temperature with the proton resonance frequency shift technique.

Figure 8A:
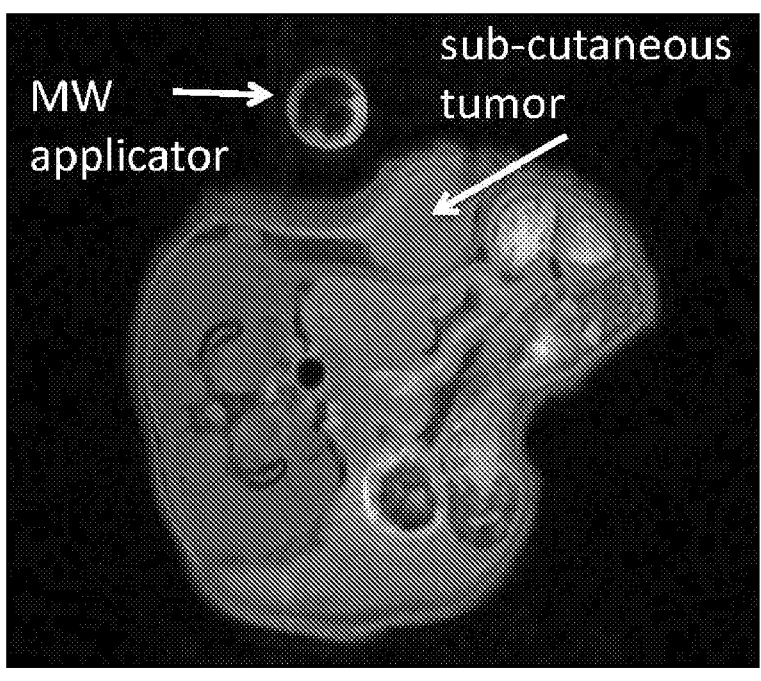
FIGS. 8(*a*) and (*b*) are MRI scanner images of mouse subjects during microwave energy application.
Figure 8B:
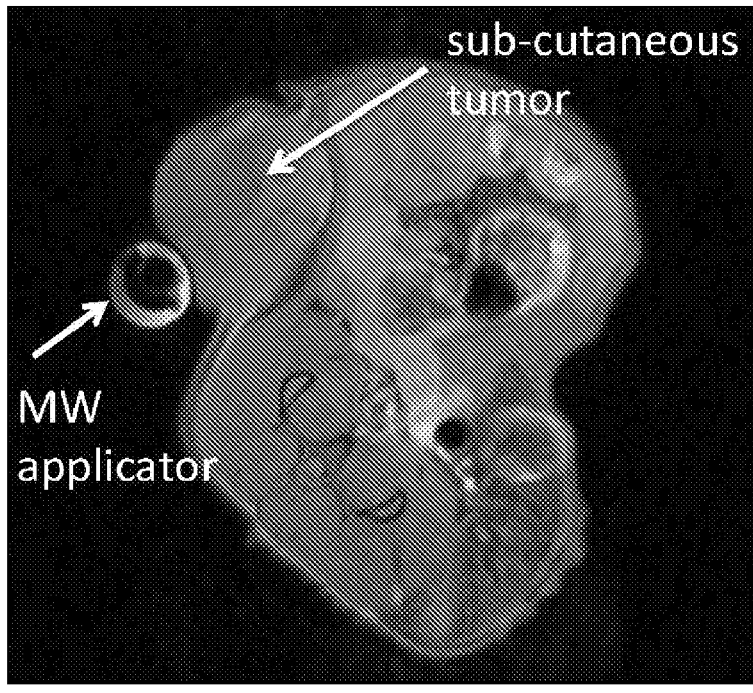

The high sensitivity of the 14 T scanner facilitated precise localization of antenna orientation and placement within the scanner as shown in MRI images of FIGS. 8(a) and (b) which were taken from two different mouse subjects. The optimized antenna yielded experimental S11<−21 dB at 2.45 GHz. MR-derived temperature maps in agar-based phantoms were validated with fiber-optic temperature measurements. Maximum error between MR thermometry and the fiber-optic temperatures measurements was less than 0.3° C. at peak temperatures increases of 8° C. with antenna input power of 8 W. There was no observable electrical artifact introduced by operation of antenna within the MR environment. Susceptibility and flow artifacts were negligible and localized to submillimeter distance from the applicator.

Example 2

The objective of this study was to design and characterize the technical efficacy of a 915 MHz phased antenna array comprised of multiple patch elements with a shared groundplane, for integration within a comfortable and wearable hyperthermia system for delivering hyperthermia to tumors positioned at varying breast locations. To account for variability in breast dimensions, 3D-hemispherical breast models of diameter 90-150 mm were considered. Target tumors 96, 98 with maximum edge lengths of 10 mm and 30 mm, as representative of stage I and stage II cancers, respectively, were evaluated. Small/large tumor targets centered at the midline of the breast, near the chest wall, and laterally positioned were investigated. See, FIG. 9. The antenna array was designed to optimize power deposited in a target area normalized to the total power deposited in the full breast.

Materials and Methods

Numerical Breast Phantom

Figures 9, 10:
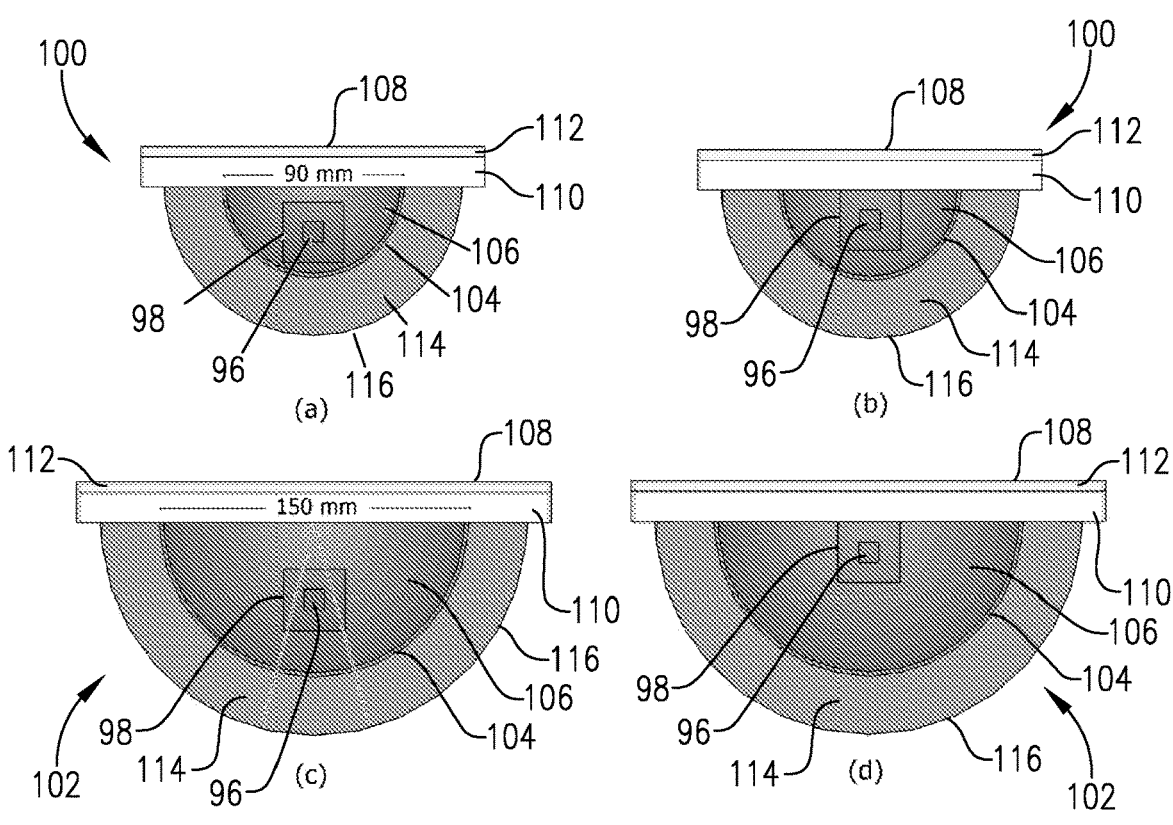
FIGS. 9(*a*) and (*b*) depict a small breast model with a target located in the breast center and near the chest wall, respectively.
FIG. 10 is a schematic diagram of an antenna element used an a phased antenna array according to the present invention.
Figure 11:
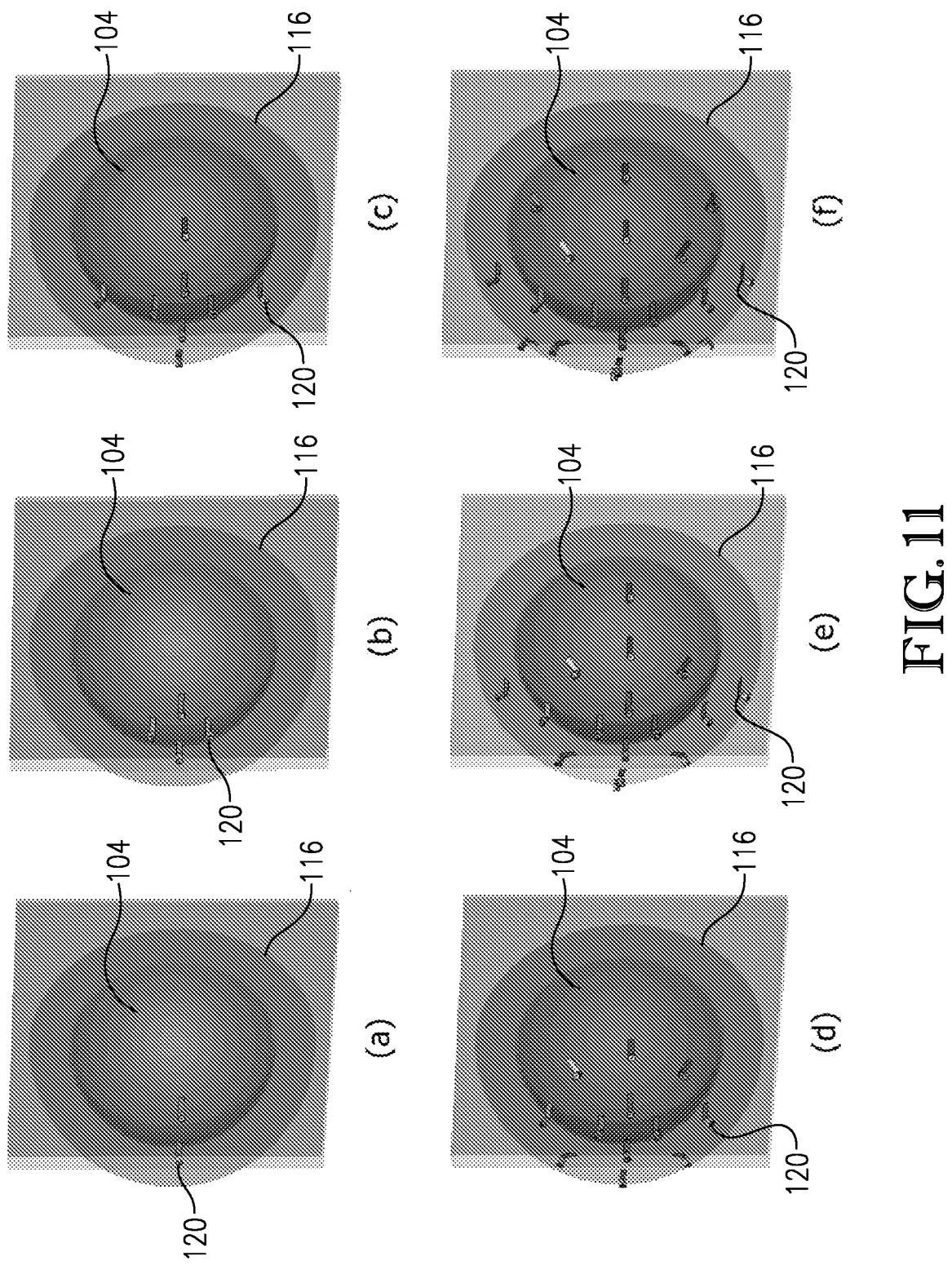
FIGS. 11(*a*)-(*f*) depict array configurations with 2, 4, 8, 12, 16, and 20 element antennas, respectively.

Optimal configuration of microwave hyperthermia breast applicator is a function of biophysical (e.g., perfusion, dielectric parameters) and dimensional (e.g., breast size, tumor size, tumor location) parameters that may vary considerably amongst patients. Thus, practical systems trade-off optimal treatment of select patient populations, with the ability to adequately treat a wide variety patients. To account for variability in breast dimensions, two numerical breast phantoms have been evaluated. The phantoms are hemispheric models 100 of outer diameter 90 mm ("small breast model") and 150 mm 102 ("large breast model") and both comprised a 2 mm thick skin layer 104 encompassing fibroglandular tissue 106. The chest wall 108, modeled as a 170 mm layer for the "small breast model" and 230 mm layer for the "large breast model" of 15 mm thick fat 110 adjacent to 5 mm thick muscle 112, terminated the top wall of the breast phantom, as shown in FIG. 9. Frequency dependent dielectric properties for water, skin, fibroglandular and fat tissue were implemented in the model, as listed in Table 1.

TABLE 1

Tissue Dielectric Properties for 915 MHz.

| Tissue | Relative permittivity, $\in_r$ | Conductivity, $\sigma$, S m$^{-1}$ | Density, $\rho$, kg m$^{-1}$ |
|---|---|---|---|
| De-ionized water | 79.95 | 0.203 | 1000 |
| Skin | 46.02 | 0.85 | 1085 |
| Fibroglandular tissue | 41.14 | 0.83 | 1050 |
| Fat | 5.45 | 0.051 | 1069 |
| Muscle | 54.99 | 0.948 | 1041 |

Target volumes of "10 mm cubic side" and "30 mm cubic side" which are representative of Stage I and Stage II breast cancers tumors located in the midline of the breast center and near the chest wall were evaluated. The centrally located tumor targets were positioned with their center at 22.5 mm and 37.5 mm from the skin in the case of the small breast model and large breast model, respectively. The tumors located near the chest wall were positioned with their center at 15 mm from the fat tissue of the chest wall.

Antenna Geometry

Array configurations with 2, 4, 8, 12, 16 and 20 patch antenna elements 120 operating at 915 MHz were evaluated. All the antenna elements shared a hemispherical ground-plane 116 concentric around the breast target. The rectangular patch elements with patch length 14 mm and patch width 3.9 mm were designed as described in Curto S. et al., "Design of a compact antenna with flared groundplane for a wearable breast hyperthermia system. Int J Hyperthermia. 2015 Oct. 3; 31(7):726-36, incorporated by reference herein in its entirety. As shown in FIG. 10, the antenna comprised a rectangular patch 122 of length L, and width W. The patch 122 is centrally aligned with the ground-plane base, and positioned at a distance h1. The antenna feed 124 is centered with respect to W, and at a distance Lo from the patch edge 126. The patch antenna to skin distance is shown as h2.

The distance between the patches and the breast skin was fixed to 25 mm for all the arrays configuration, as preliminary investigated indicated this distance showed a compromise between power absorption and wearability and comfort of the applicator. The water bolus 114 filled all the cavity enclosed by the hemispherical groundplane, breast and chest wall. Deionized water completely filled the water bolus so as to improve the matched impedance, reduce the size of the applicator and cool both the antenna and surface of the skin.

The elements were positioned on the applicator circumference along orthogonal arcs (the x-axis, the y-axis and located in the diagonal between the x-axis and y-axis as depicted in FIG. 10). All the patch elements were located at constant distance defined by the parameter $\alpha_{inter\_antenna}$ (angular separation) as shown in FIG. 9. The inter-antenna distance was analyzed to obtain the greatest power absorption in the desired target without compromising the impedance matching of the individual elements. A maximum acceptable value of reflected power (S11) was set to −8.5 dB, to balance between antenna efficiency and the ability to closely position multiple antenna elements. Positioning elements at greater distances diminishes the ability to focus energy, while positioning the elements at closer distances generates near field interferences that would compromise the impedance matching of the system. Circumferential separation angles of 10°, 11.25°, 22.5°, 37.75°, 45°, 56.25° and 67.5° were evaluated. While lower angles allow the implementation of configurations with larger number of elements and potentially capable of steering energy in a variety of locations, they increase the complexity to the system. For configurations of 8-elements and 12-elements the largest possible angle is 22.5°, for configurations with 16-elements and 20-elements, the largest possible angle is 11.25°.

Evaluation of Proposed Designs

The average power absorption (PA) was evaluated in the target volumes and in the full breast volume using Equation 1

$$PA = \frac{\sigma|\vec{E}|^2}{2} \ [W/m^3] \tag{1}$$

where $\sigma$ [S/m] is the electrical conductivity of the tissue, |$\vec{E}$| [V/m] is the complex electric field vector and $\rho$ [kg/m$^3$] is the mass density. The system performance is expressed in terms of the $\alpha$PA ratio as defined in Equation 2

$$\propto PA = \frac{\frac{PA_{targ}}{targ\_volume}}{\frac{PA_{breast}}{breast\_volume}} \tag{2}$$

where $PA_{targ}$ is the averaged power absorbed in the target volume ("10 mm side cubic" or "30 mm side cubic"), target_volume is the volume enclosed of the "10 mm side cubic" or "30 mm side cubic", and $PA_{breast}$ is the averaged power absorbed in the full breast ("small breast model" or "large breast model") and breast_volume is the volume enclosed for the "small breast model" or "large breast model."

Electromagnetic simulations were performed using CST Microwave Studio on a 3.0 GHz PC with 16 GB RAM. Memory requirements and simulation times ranged from 691 MB and 39 min for the "small breast model" with the 2-element antenna array configuration to 13 GB and 7 h 56 min for the "large breast model" with the 20-element antenna array configuration. Phased array computations were performed using Matlab (R2015).

Experimental Evaluation and Validation

Figure 12:
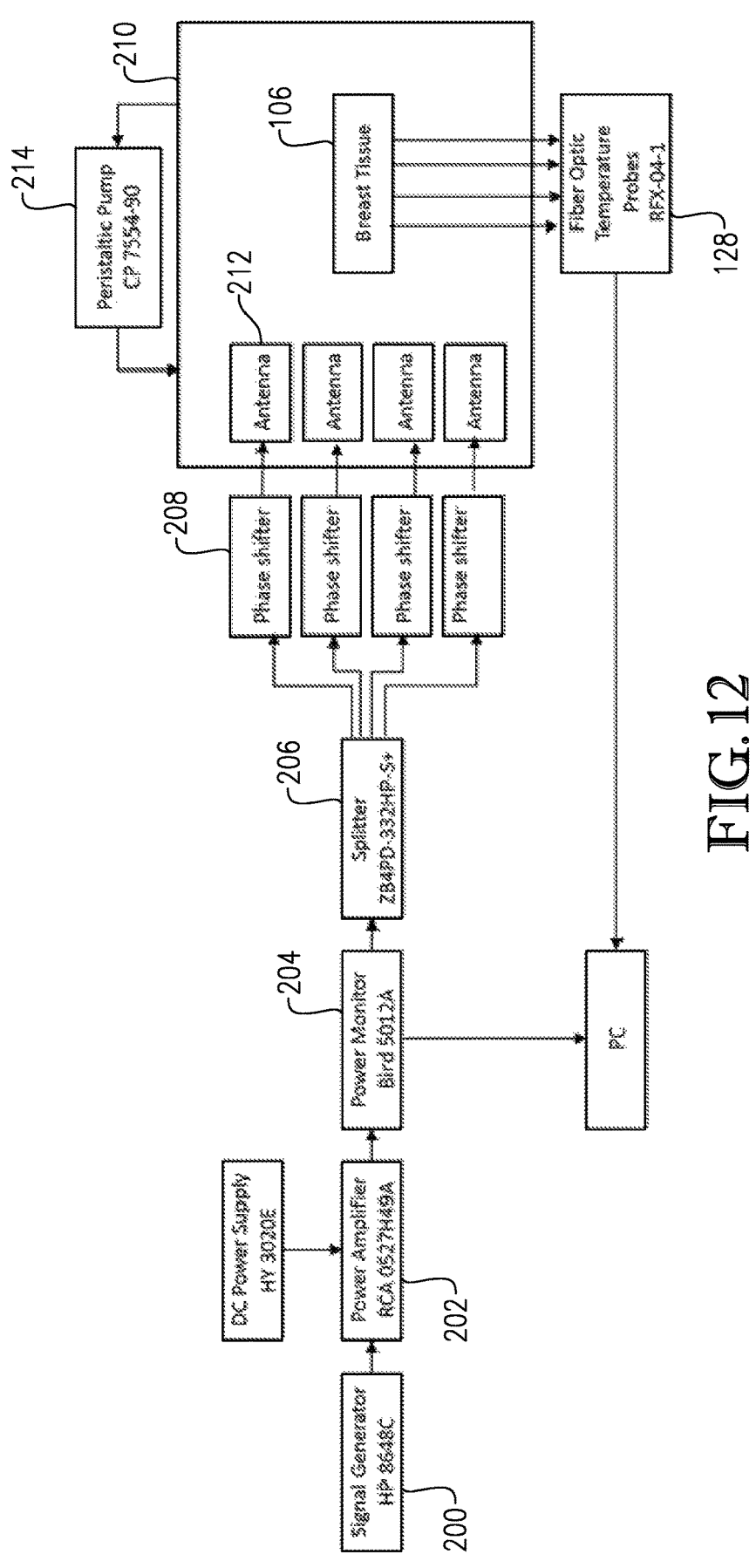
FIG. 12 schematically depicts the set-up for the experimental assessment of a phased array applicator in ex vivo tissue.
Figure 13A:
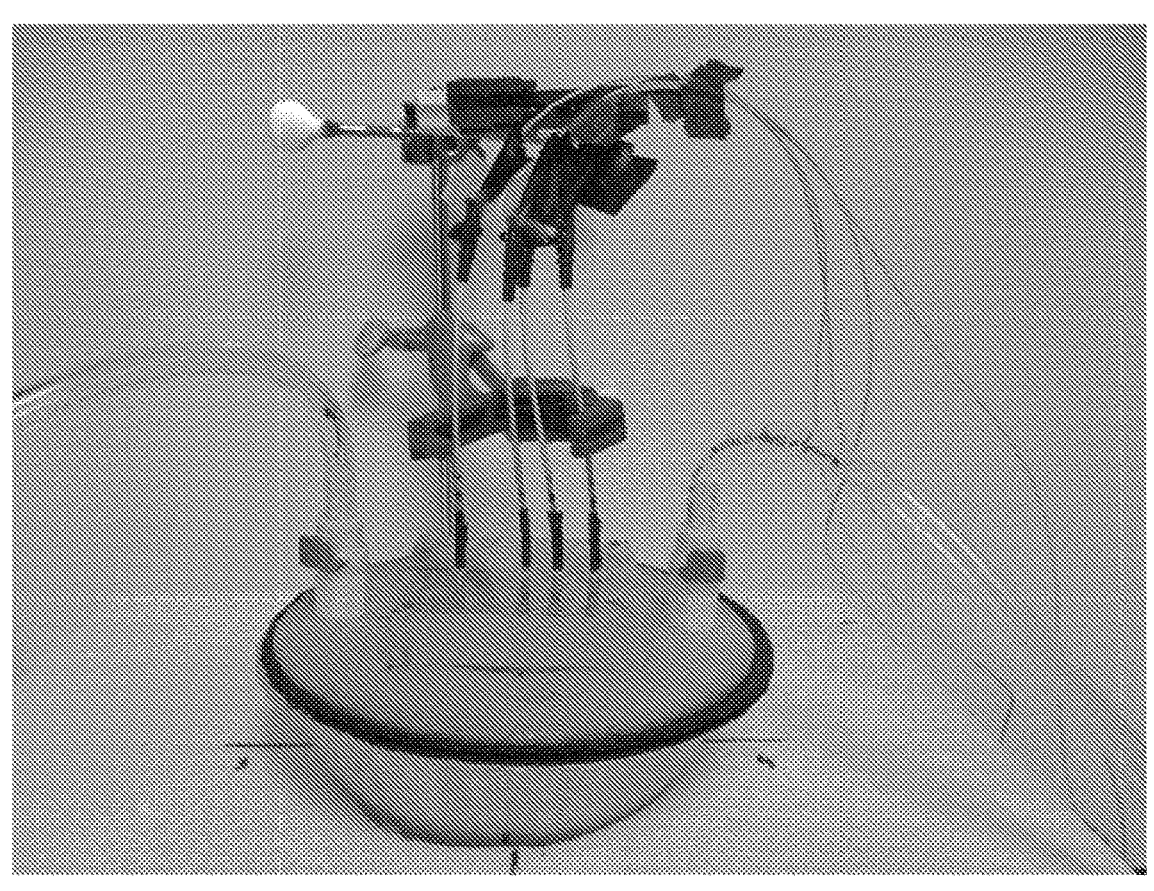
FIG. 13(*a*) is a photograph of the experimental phased antenna array used in the ex vivo experiments.
Figure 13B:
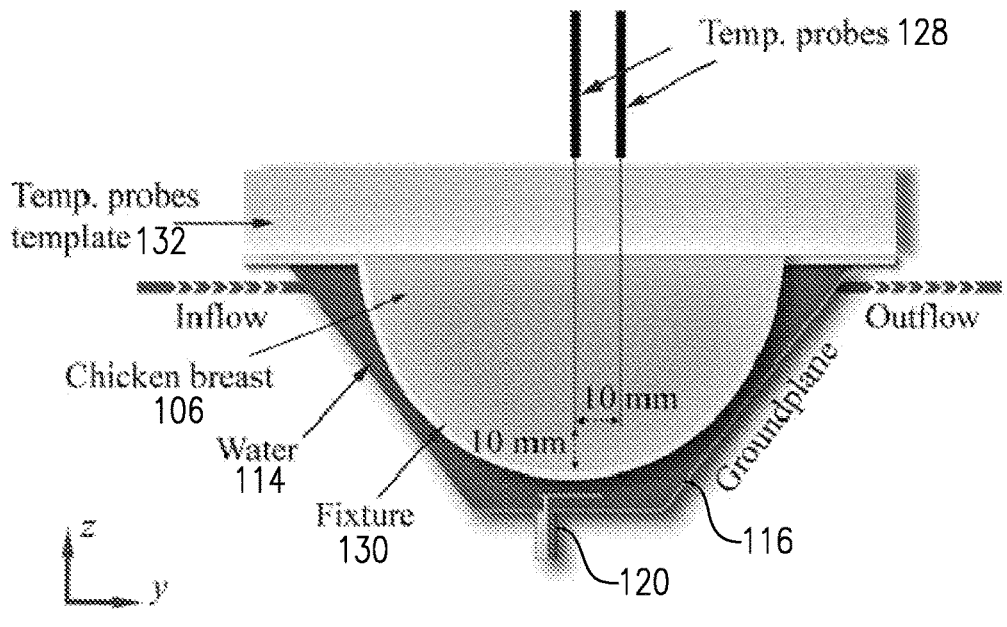

The proposed 4-element array configuration with hemispherical groundplane was fabricated, employing optimized antenna dimensions identified from simulations. The patches and groundplane were implemented with 0.127 mm thick copper sheets (McMaster-Carr, Elmhurst, IL). 50$\Omega$ SMA female connectors (PE4099, Pasternack Enterprise, Irvine, CA) were used to feed the antennas. The broadband reflection coefficient of the fabricated antenna was measured when in proximity to a tissue phantom of ex vivo chicken breast. Heating experiments in the tissue phantom were performed with the setup illustrated in FIG. 12 to measure the transient temperature profiles induced by the proposed applicator. The microwave hyperthermia system comprises a signal generator 200, power amplifier 202, power monitor 204, 4-channel power divider 206, 4 manually controlled phase shifters 208, and the applicator 210 comprising 4 antennas 212. Chicken breast samples 106 were heated to ~32° C. in a temperature controlled bath before performing the heating experiments and then positioned in a 3D-printed 1.5 mm thick PTFE fixture 130. Fiber-optic temperature probes 128 (Neoptix RFX-04-1, Canada) guided with a PTFE template 132 were placed within the tissue sample 106 as shown FIG. 13. Room temperature water was circulated through the system at a flow rate of 5 ml/s with a peristaltic pump 214 (Cole-Parmer, 7554-90, IL). Applied input power was set to constant 7.5 W per antenna during the 10 min treatment. Experiments were performed with applied input power with constant phase to reach high power absorption in a centrally located target at 22.5 mm from the skin surface and with the optimized phases values to generate a hotspot in a target located at an offset of 22.5 mm for the midline of the breast and at a distance of 22.5 mm from the breast skin. Heating experiments were performed in quadruplicate.

Results

Evaluation of Angular Separation Between Antenna Elements

Figure 14:
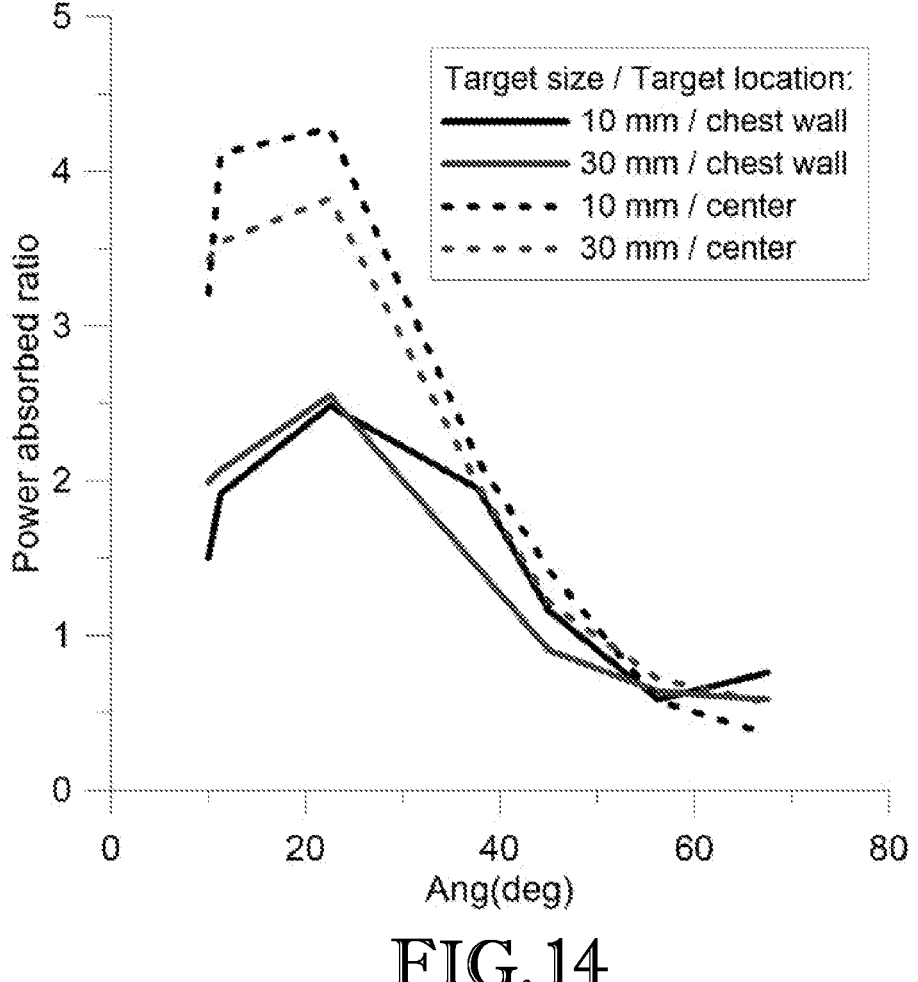
FIG. 14 is a graph of the power absorbed ratio for the "10 mm cubic side" target and "30 mm cubic side" target located at the center and near the chest wall of the small breast model for different angular separation of the 4-element array.

Reduced angular separation between antenna elements facilitates the implementation of a high number of elements to steer the energy at different breast locations. The antennas have to be close enough to create constructive electromagnetic interferences at the target locations and sufficiently distant to avoid compromising individual impedance matching. FIG. 14 illustrates the αPA ratio for a 4 element array as a function of the angular separation for the "10 mm side" and the "30 mm side" targets located at the center and close to the chest wall of the "small breast model". The evaluated angular separation are 10°, 11.25°, 22.5°, 37.75°, 45°, 56.25° and 67.5°.

Figure 15A:
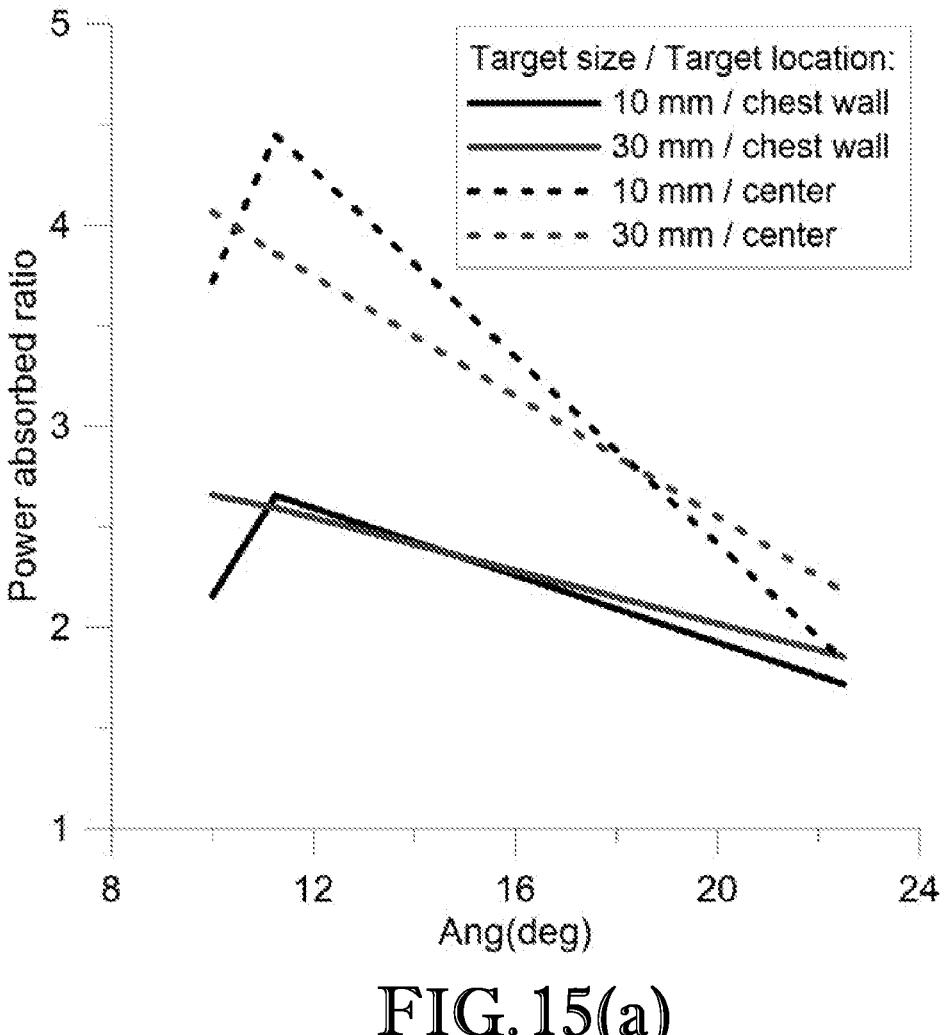
FIGS. 15(*a*) and (*b*) are graphs of the power absorbed ratio for the "10 mm cubic side" target and "30 mm cubic side" target located at the center and near the chest wall of the small breast model for different angular separation (10°, 11.25° and 22.5°) of the 8-element array configuration and the 12-element array configuration, respectively.
Figure 15B:
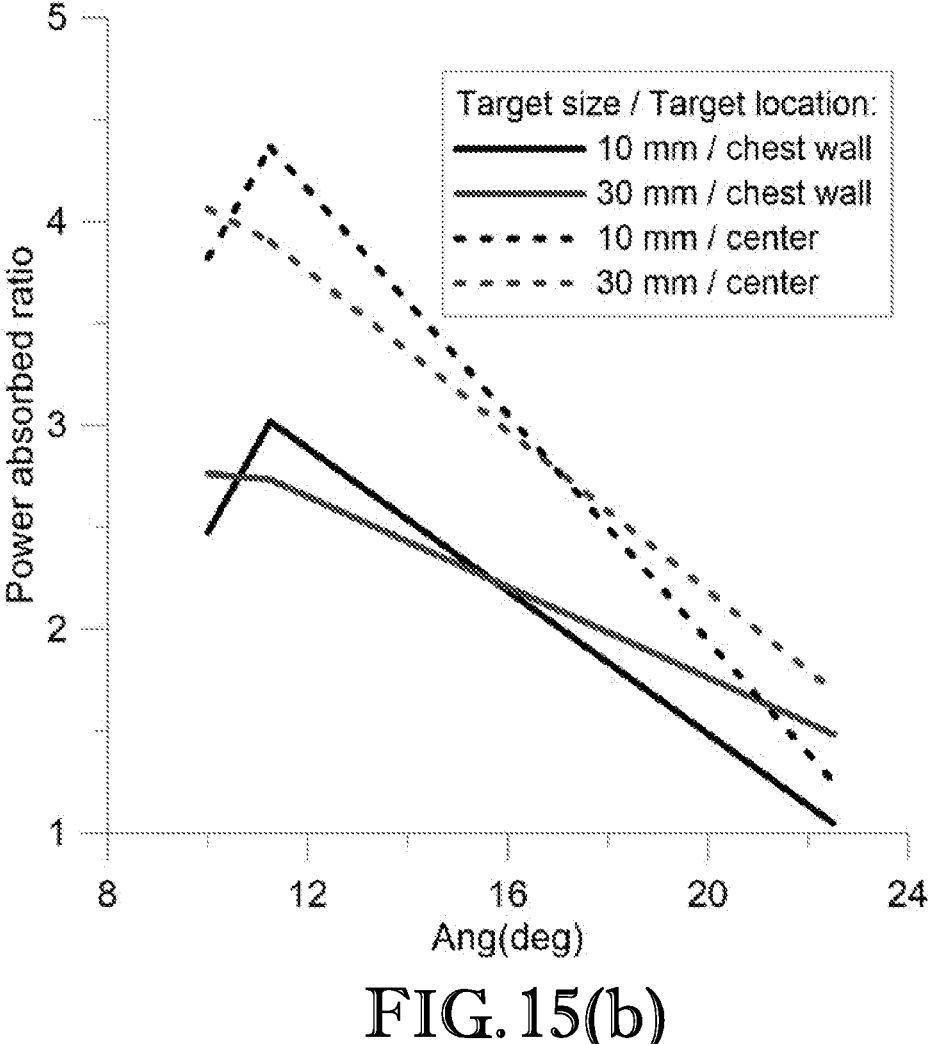

FIGS. 15(a) and (b) illustrate the αPA ratio for 8-element and 12-element array configurations, respectively, as a function of the angular separation for the "10 mm side" and the "30 mm side" targets located at the center and close to the chest wall of the "small breast model". The evaluated angular separation are 10°, 11.25° and 22.5°. These are the largest angular separation for this hemispherical breast model.

Evaluation of Number of Elements in the Array Configuration

Figure 16A:
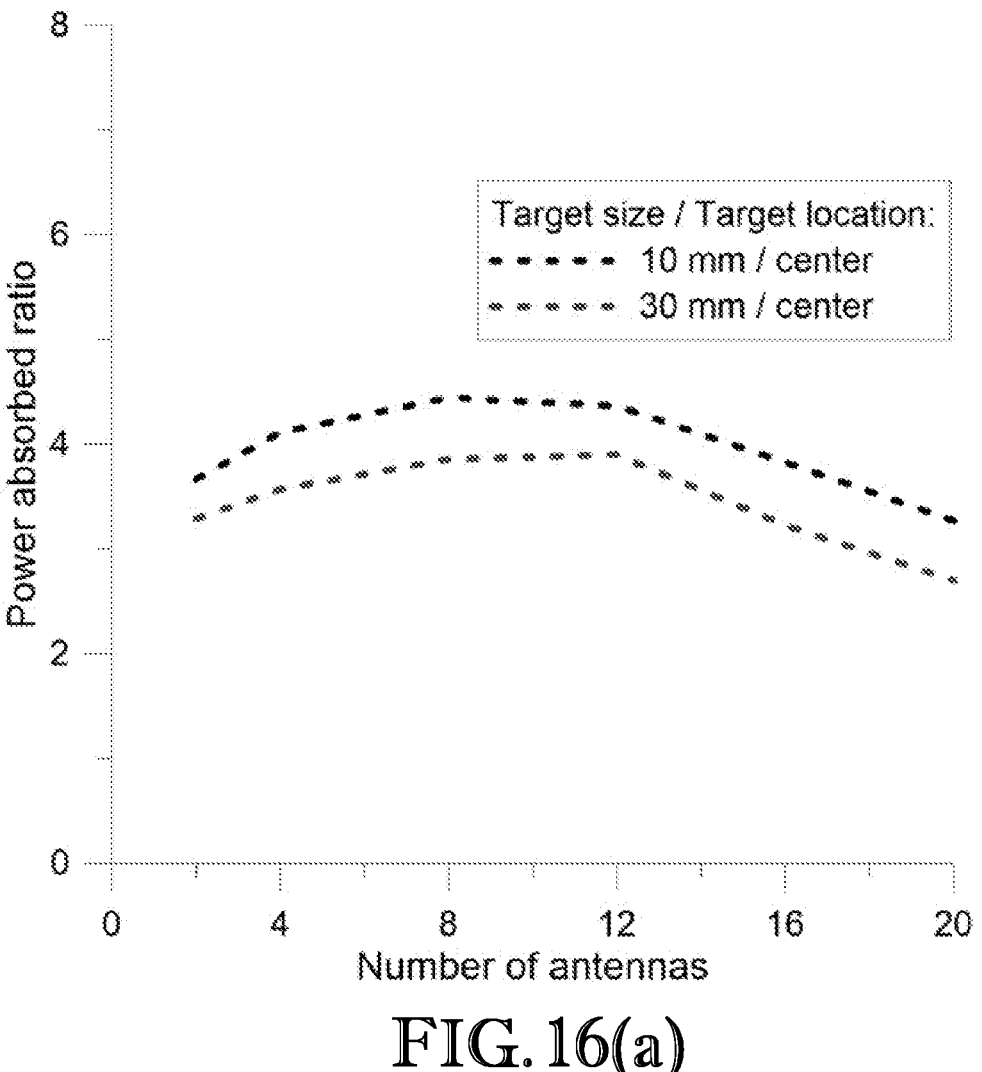
FIGS. 16(*a*) and (*b*) are graphs of the power absorbed ratio for the "10 mm cubic side" target and "30 mm cubic side" target located at the center and near the chest wall, respectively, of the small breast model for different number of antenna element configurations and angular separation 11.25°.
Figure 16B:
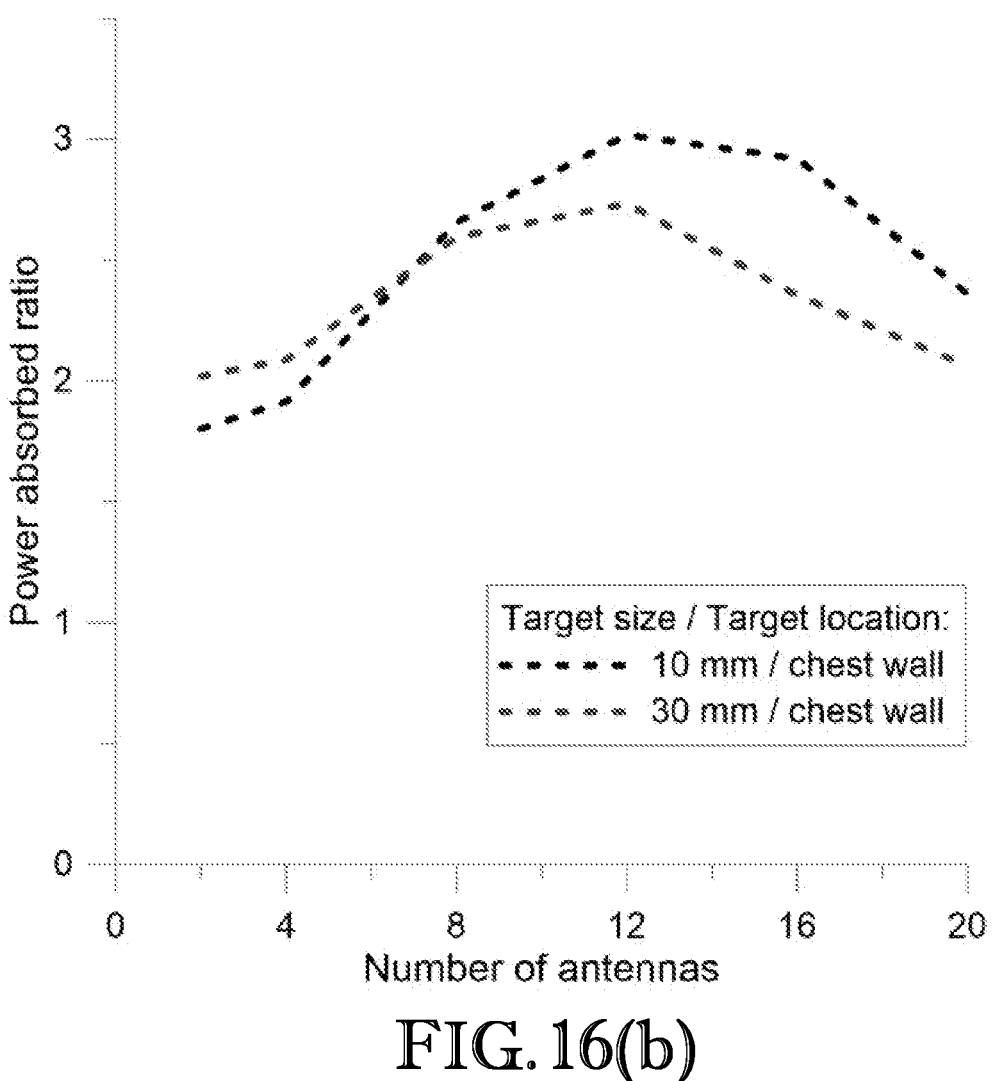
Figure 17:
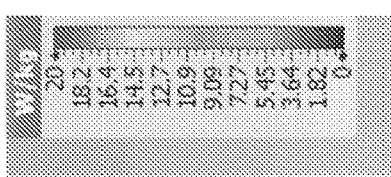
FIGS. 17(*a*)-(*f*) show SAR cross-sections on the planes −xz of the small breast model and antenna array configurations of 2, 4, 8, 12, 16 and 20 elements, respectively, with an input power of 1 W and constant phase.
Figure 17:
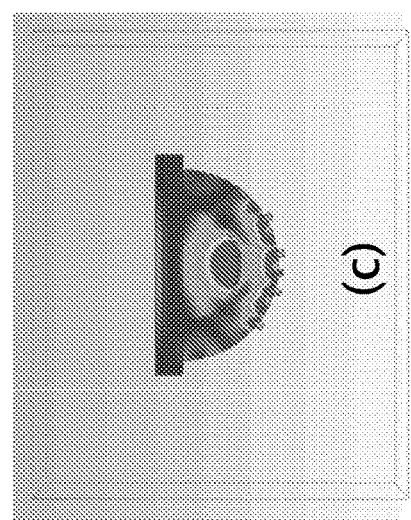
Figure 17:
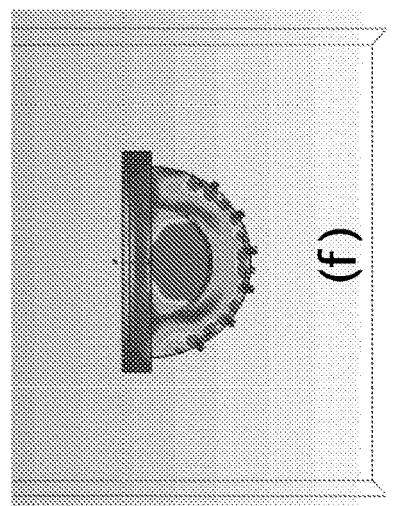
Figure 17:
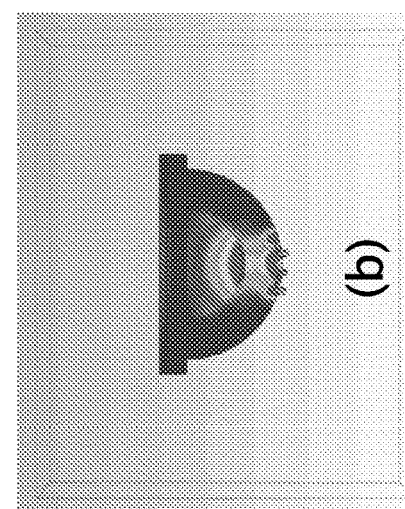
Figure 17:
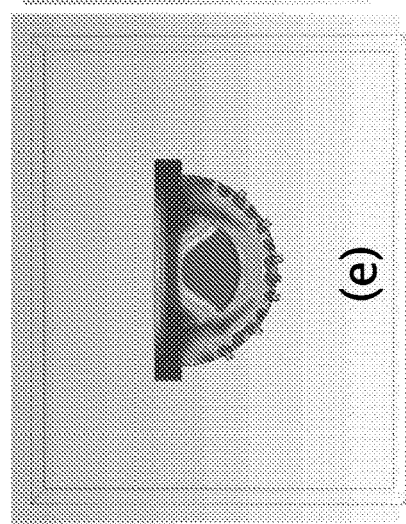
Figure 17:
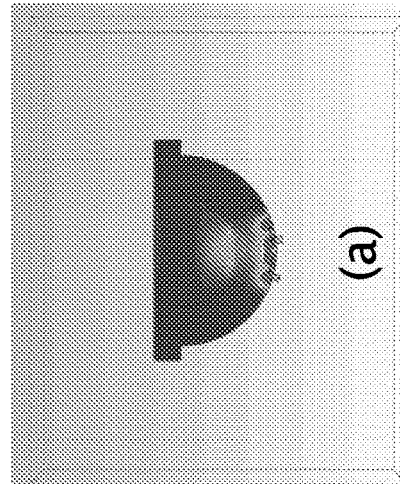
Figure 17:
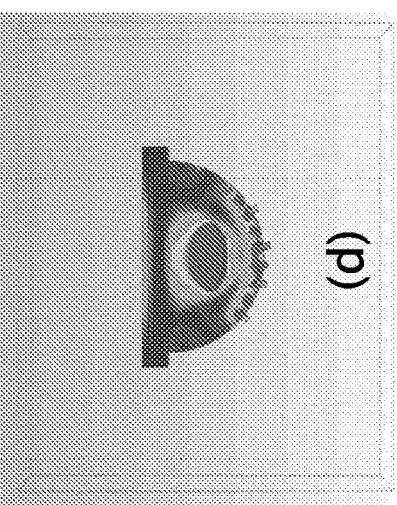

FIGS. 16(a) and (b) illustrate the αPA ratio as a function of number of elements for the "10 mm side" and the "30 mm side" targets located at the center and close to the chest wall, respectively, of the "small breast model" for configurations with angular separation of 11.25°. Array configurations of 2, 4, 8, 12 and 20-element were evaluated.

The SAR cross-sections on the planes –xz of the "small breast model" and antenna array configurations of 2, 4, 8, 12, 16 and 20 elements with an input power of 1 W and constant phase is shown in FIGS. 17(a)-(f), respectively.

Evaluation of Largest Breast Model

Figure 18A:
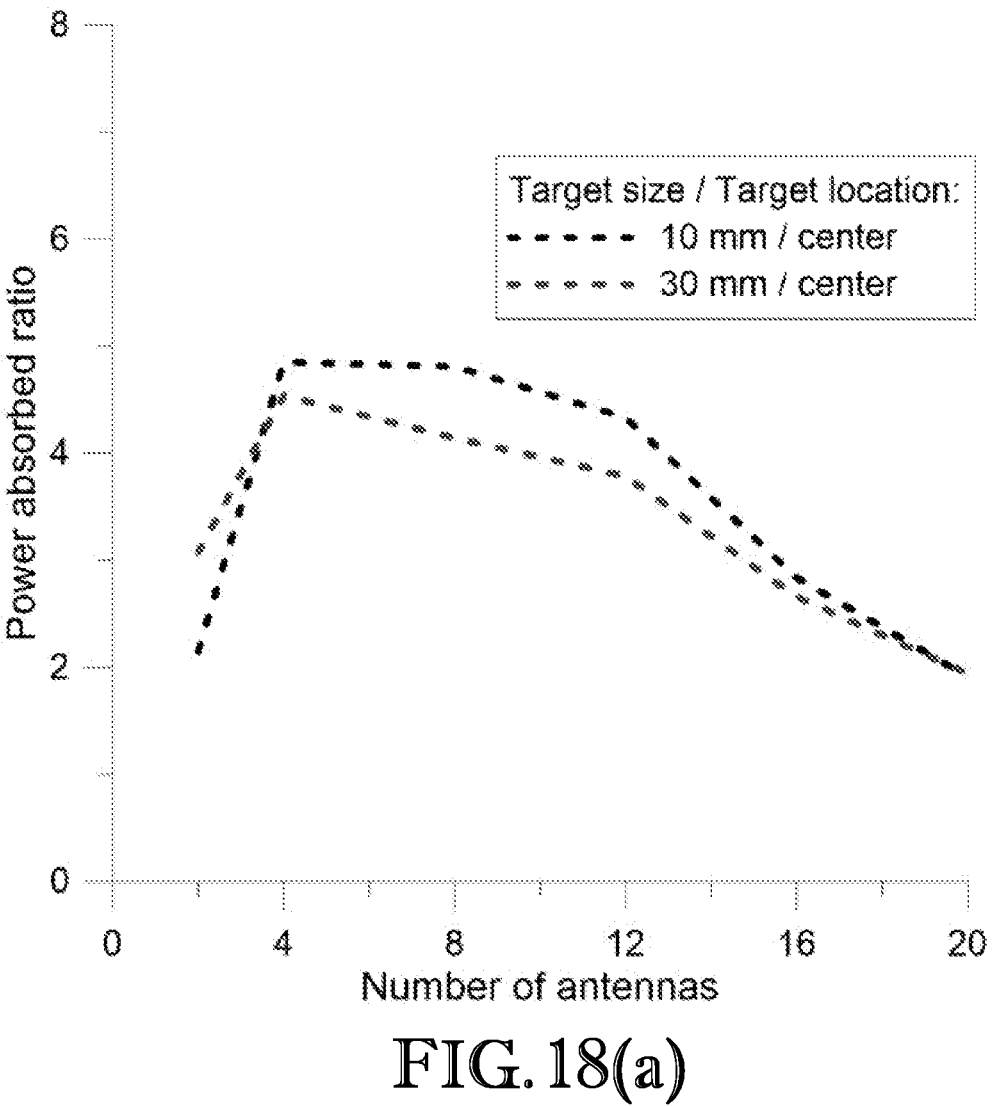
FIGS. 18(*a*) and (*b*) are graphs of power absorbed ratio for the "10 mm cubic side" target and "30 mm cubic side" target located at the center and near the chest wall, respectively, of the large breast model for different number of antenna element configurations and angular separation 11.25°.
Figure 18B:
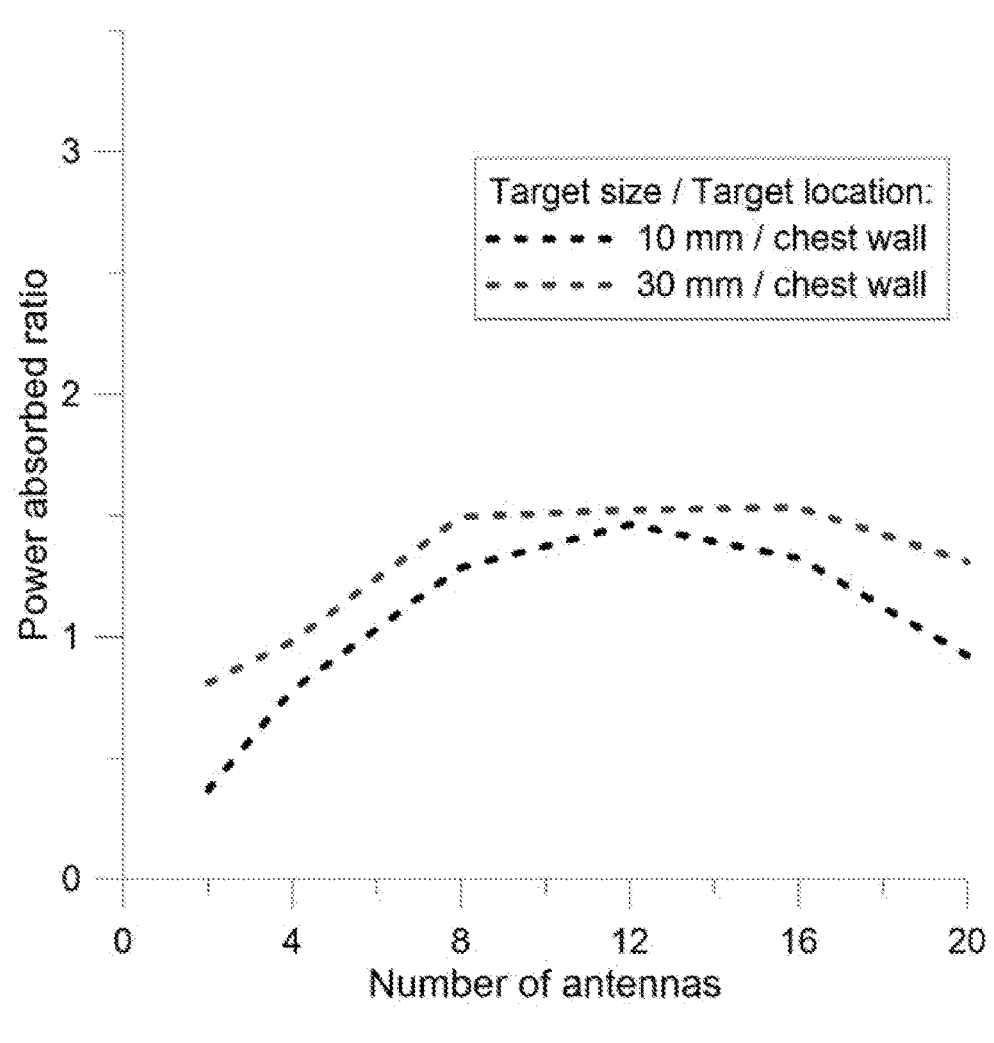

FIGS. 18(a) and (b) illustrate the αPA ratio as a function of number of elements for the "10 mm side" and the "30 mm side" targets located at the center and close to the chest wall, respectively, of the large breast models for configurations with angular separation of 11.25°. Array configurations of 2, 4, 8, 12 and 20-elements were evaluated.

Figure 19:
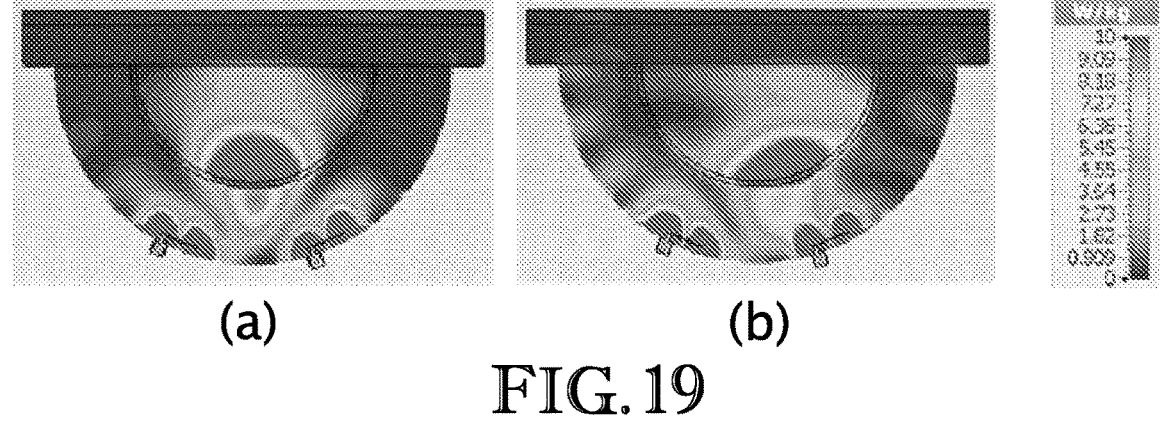
FIGS. 19(*a*) and (*b*) show SAR cross-sections on the −xz plane with elements with constant phase and optimized phase, respectively, to create a hotspot in a laterally located target.

FIGS. 19(a) and (b) show simulated SAR distributions in the plane –xz for the 4 element configuration with (a) constant phase with the objective of generating a hotspot in a target located at the midline of the breast and (b) optimized phases (84.5°, 84.5°, 123°, 0°) with the objective of steering the energy deposition to a target located at 22.5 mm from the skin and with and offset of 22.5 mm from the breast midline.

Experimental Evaluation

Figure 20:
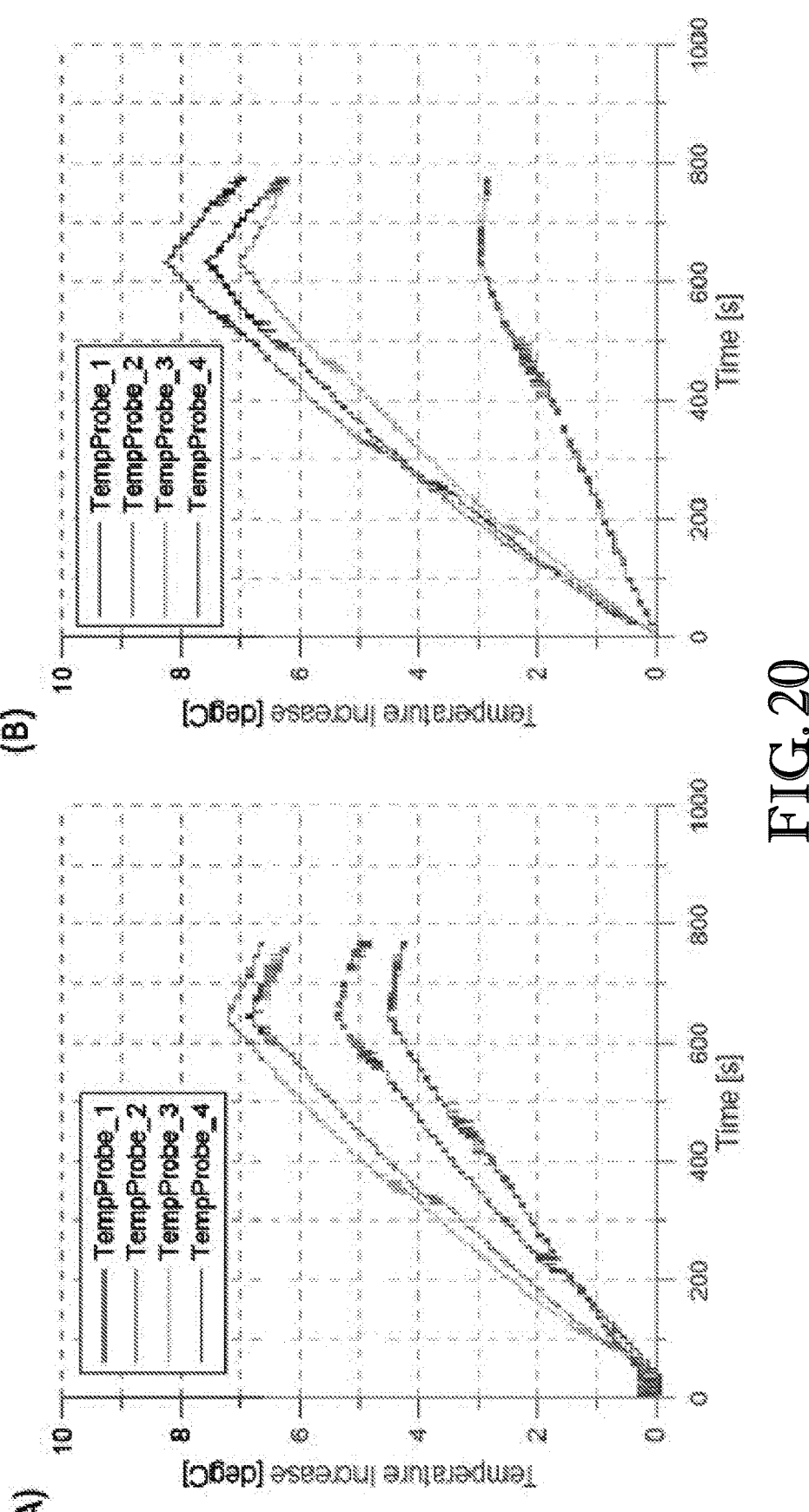
FIGS. 20(*a*) and (*b*) are graphs depicting transient temperature monitoring of the phased array with the 4-element antennas with constant phase (a), and phased optimized (b).

FIGS. 20(a) and (b) show experimentally measured (n=4) transient temperature profiles during heating experiments performed in chicken breast, while applying a input power of 7.5 W per antenna with all the antennas fed with constant phase (FIG. 20(a)) and with optimized phase to steer the energy in a target offset 22.5 mm from the breast midline (FIG. 20(b)).

Discussion

This study was initiated to design and evaluate the feasibility of a wearable phased array system for hyperthermia treatment of Stage I and Stage II cancers at different locations in the intact breast. Simulations were employed to evaluate different array configurations to steer electromagnetic energy in targets of different sizes and locations. When evaluating inter-antenna spacing for a 4-element array, increasing angular separation from 10° to 22.5° increased the αPA for targets located in the center of the breast and near the chest wall for both the "10 mm cubic side" target and "30 mm cubic side" targets for the small breast model. Further increases of the inter-antenna angular space decreased the energy deposited within the target. When evaluating inter-antenna angular spacing for 8- and 12-element arrays, the highest αPA was found at 11.25° for the "10 mm cubic side" target and at 10° for "30 mm cubic side" target. However, positioning the antenna elements at 10° or less produced poor antenna impedance matching, with a S11 below the –8.5 dB maximal acceptable value.

Evaluating the influence of the number of elements for the small breast model with an inter-antenna angular separation of 11.25° indicated that increasing the number of elements from 2 to 8 increases αPA in the "10 mm cubic side" target located in the center of the breast model, while configurations with larger number of elements reduced the αPA. For the "30 mm cubic side" target, increasing the number of elements from 2 to 12 increased αPA, and configurations with larger number of elements reduced αPA. Increasing from 4 to 12 elements generated an increase on the αPA of 6.1% and 9.24%, respectively, for the "10 mm cubic side" targets and "30 mm cubic side" targets. When the targets are located near the chest wall, for both the targets volumes the largest αPA were found for configurations with 12 elements. In this case, increasing from 4 to 12 elements generated an increase on the αPA of 57.6% and 30.9%, respectively for "10 mm cubic side" target and "30 mm cubic side" target. In general, for the "small breast model" and targets located in the center of the breast, increasing from 4 to 12 elements will significantly increase the complexity of the system with a slight increase in the αPA, however for targets located near the chest wall the highest αPA obtained with configurations with 12 elements suggest that in this case it would be beneficial using this elevated number of antenna elements at the expense of adding complexity to the system.

The arrays tested utilized a hemispherical groundplane concentric around the breast which yielded a SAR confined within the groundplane and focused into the tissue with a defined central hotspot. The angular separation of 11.25° provides an inter-antenna distance to enhance energy deposition due to constructive antenna interferences.

Evaluating the influence of number on antenna elements for the large breast model on the αPA showed that increasing the number of elements from 2 to 4 increases 125.6% in the "10 mm side cubic" target and 47.5% in the "30 mm cubic side" target located in the center of the large breast model, while configurations with larger number of elements reduced αPA. When the targets were located near the chest wall, for the "10 mm cubic side" target the largest αPA were found for configurations with 12-elements, and for the "30 mm cubic side" target, the largest αPA were found for configurations with 16 elements (only 0.5% increase in the αPA with 16-elements respect the 12-elements configuration). In this case, increasing from 4 to 12 elements generated an increase on the αPA of 86.8% and 54.8%, respectively for "10 mm cubic side" targets and the "30 mm cubic" side targets. For large breast models and targets located in the center of the breast, array configurations of 4-elements are preferable due a highest αPA and reduced system complexity compared with configurations with higher number of elements. For targets located near the chest wall the highest αPA obtained with configurations with 12 elements suggest that in this case it would be beneficial using this elevated number of elements.

The optimum inter-antenna angular separation for a 4-element array configuration for the "small breast model" was found to be 22.5° and an applicator with this characteristics was fabricated to evaluate the steering capabilities of the design. A phase algorithm was implemented to steer energy in laterally located targets. The optimized phases for this 4-element array configuration were found to be 84.5°, 84.5°, 123°, 0°. Measured reflection coefficient in ex vivo chicken breast was in good agreement with simulations. The measured temperature profiles illustrate the ability of the proposed applicator design to treat targets located in variable positions within the intact breast when applying relatively low input power levels (7.5 W per antenna element). Measured temperature profiles were in good agreement with SAR simulations.

For the small breast model, using an array configuration with 8-elements, spaced 11.25°, provides similar performance for small/large targets near the chest wall, while arrays configurations with 4- to 12-elements provides similar performance for small/large targets in the center of the breast. For the large breast model, using an array configuration with 12-elements, spaced 11.25°, provides similar performance for small/large targets near the chest wall, while arrays configurations with 4-elements provides similar performance for small/large targets in the center of the breast.

We claim:

1. A method of delivering hyperthermia treatments to a subject's breast tissue comprising:

positioning at least a portion of the subject's breast within a magnetic resonance imaging scanner that is operable to generate an internal image of the portion of the subject's breast and provide thermometry data for the portion of the subject's breast;

positioning a microwave applicator adjacent to the subject's breast tissue that is targeted for heating, the microwave applicator having a cup-like configuration and a concave surface defining a cavity that is adapted to receive the subject's breast tissue therein and being configured for emitting electromagnetic energy therefrom sufficiently strong to create electromagnetic interference that causes the heating of the breast tissue, the microwave applicator comprising a phased antenna array including a plurality of antenna elements having a shared groundplane, the plurality of antenna elements being arranged on the microwave applicator along a plurality of arcs that extend along the concave surface and intersect an apex thereof, each of the plurality of antenna elements being spaced along the arcs such that adjacent antenna elements on an arc are angularly separated by a separation angle of at least 10 degrees up to 30 degrees, the separation angle being defined by lines intersecting two center points on the adjacent antenna elements and a center of curvature of the concave surface, wherein the plurality of antenna elements are configured to adjust a location of the electromagnetic interference along an x-axis, y-axis, and z-axis by shifting a phase of one or more antenna element of the plurality of antennas such that two or more of the plurality of antenna elements have different phases;

emitting the electromagnetic energy from the applicator and directing the electromagnetic energy toward the breast tissue targeted for the heating;

imaging the portion of the subject's breast with the magnetic resonance imaging scanner and generating the thermometry data for the imaged portion of the subject's breast;

transmitting the image and the thermometry data to a controller that is operable to analyze, in real time, the image received from the scanner and to generate a signal used to control the amount of the electromagnetic energy emitted from the applicator;

analyzing, with the controller, the image received from the scanner; and generating, with the controller, the signal and using the signal to control the amount of and/or direction of the electromagnetic energy emitted from the applicator.

2. The method of claim 1, wherein the magnetic resonance imaging scanner is at least a 1.5 tesla scanner.

3. The method of claim 1, wherein the magnetic resonance imaging scanner is an ultra-high field scanner.

4. The method of claim 1, further comprising using the image generated by the magnetic resonance imaging scanner to adjust the position of the microwave applicator.

5. The method of claim 1, further comprising circulating a cooling fluid within the applicator so as to reduce a temperature of the applicator.

6. The method of claim 1, wherein the signal generated by the controller is used to command a reduction in the electromagnetic energy emitted from the applicator.

7. The method of claim 1, wherein signal generated by the controller used to command an increase in the electromagnetic energy emitted from the applicator.

8. A method of delivering hyperthermia treatments to a subject's breast tissue comprising:

positioning at least a portion of the subject's breast within a magnetic resonance imaging scanner that is operable to generate an internal image of the portion of the subject's breast and provide thermometry data for the portion of the subject's breast;

positioning a microwave applicator adjacent to the subject's breast tissue that is targeted for heating, the microwave applicator being configured to maintain the subject's breast tissue in a substantially hemispherical form during delivery of the hyperthermia treatment, the microwave applicator being configured for emitting electromagnetic energy therefrom sufficiently strong to create electromagnetic interference that causes the heating of the targeted tissue, the microwave applicator comprising a water bolus configured to surround at least a portion of the subject's breast, the microwave applicator comprising a phased antenna array including a plurality of antenna elements having a shared groundplane and arranged on the microwave applicator along a plurality of arcs that extend along the concave surface from an apex of the concave surface, wherein the plurality of antenna elements are configured to adjust a location of the electromagnetic interference along an x-axis, y-axis, and z-axis by shifting a phase of one or more antenna element of the plurality of antenna elements;

emitting the electromagnetic energy from the applicator and directing the electromagnetic energy toward the tissue targeted for the heating by shifting the phase of the one or more antenna element of the plurality of antenna elements relative to an adjacent antenna element spaced apart along a shared one of the plurality of arcs such that two or more of the plurality of antenna elements have different phases;

imaging the portion of the subject's breast with the magnetic resonance imaging scanner and generating the thermometry data for the imaged portion of the subject's breast;

transmitting the image and the thermometry data to a controller that is operable to analyze, in real time, the image received from the scanner and to generate a signal used to control the amount of the electromagnetic energy emitted from the applicator;

analyzing, with the controller, the image received from the scanner; and generating, with the controller, the signal and using the signal to control the amount of and/or direction of the electromagnetic energy emitted from the applicator.

9. The method of claim 8, further comprising using the signal generated by the controller to adjust the phase of the one or more antenna element of the plurality of antenna elements to change the location of the electromagnetic energy emitted toward the breast tissue.

10. The method of claim 8, further comprising circulating a cooling fluid within the applicator so as to reduce a temperature of the applicator and skin of the subject's breast.

11. The method of claim 8, wherein the signal generated by the controller is used to command a reduction in the electromagnetic energy emitted from the applicator.

12. The method of claim 8, wherein signal generated by the controller used to command an increase in the electromagnetic energy emitted from the applicator.

* * * * *